US00RE47266E

(19) United States
(12) Reissued Patent
DiMauro et al.

(10) Patent Number: US RE47,266 E
(45) Date of Reissued Patent: Mar. 5, 2019

(54) LIGHT-BASED IMPLANTS FOR TREATING ALZHEIMER'S DISEASE

(71) Applicant: DEPUY SYNTHES PRODUCTS, INC., Raynham, MA (US)

(72) Inventors: Thomas DiMauro, Southboro, MA (US); Mohamed Attawia, Holmdel, NJ (US); Sean Lilienfeld, Sharon, MA (US); Chantal Holy, Somerville, MA (US); Jeffrey K. Sutton, Medway, MA (US); Michael Ward, Irvine, CA (US)

(73) Assignee: DePuy Synthes Products, Inc., Raynham, MA (US)

(21) Appl. No.: 15/254,116

(22) Filed: Sep. 1, 2016

Related U.S. Patent Documents

Reissue of:
(64) Patent No.: 8,821,559
Issued: Sep. 2, 2014
Appl. No.: 11/214,445
Filed: Aug. 29, 2005

U.S. Applications:
(60) Provisional application No. 60/661,629, filed on Mar. 14, 2005.

(51) Int. Cl.
*A61B 5/06* (2006.01)
*A61N 5/06* (2006.01)

(52) U.S. Cl.
CPC ..... *A61N 5/0601* (2013.01); *A61N 2005/063* (2013.01); *A61N 2005/0651* (2013.01); *A61N 2005/0659* (2013.01); *A61N 2005/0661* (2013.01)

(58) Field of Classification Search
USPC ..... 128/898
See application file for complete search history.

(56) References Cited

U.S. PATENT DOCUMENTS

| | | | | |
|---|---|---|---|---|
| 2,227,422 | A | 1/1941 | Boerstler | |
| 4,105,034 | A | 8/1978 | Shalaby | |
| 4,130,639 | A | 12/1978 | Shalaby | |
| 4,140,678 | A | 2/1979 | Shalaby | |
| 4,141,087 | A | 2/1979 | Shalaby | |
| 4,205,399 | A | 6/1980 | Shalaby | |
| 4,208,511 | A | 6/1980 | Shalaby | |
| 5,270,300 | A | 12/1993 | Hunziker | |
| 5,331,969 | A * | 7/1994 | Silberstein | 600/544 |
| 5,445,608 | A | 8/1995 | Chen | |
| 5,464,929 | A | 11/1995 | Bezwada | |

(Continued)

FOREIGN PATENT DOCUMENTS

| | | |
|---|---|---|
| RU | 2200041 | 3/2003 |
| RU | 2222362 | 1/2004 |

OTHER PUBLICATIONS

Yaroslavsky, Optical Properties of Selected Native and Coagulated human Brain Tissue in Vitro in the Visible and Near Infrared Spectral Range, Phys. Med. Biol., 2002, pp, 2059-2073, vol. 47.

(Continued)

*Primary Examiner* — Cary E Wehner
(74) *Attorney, Agent, or Firm* — Nutter McClennen & Fish LLP

(57) ABSTRACT

An intracranial, light-emitting implant for providing therapy to a patient having Alzheimer's Disease.

14 Claims, 7 Drawing Sheets

(56) References Cited

U.S. PATENT DOCUMENTS 5,571,152 A 11/1996 Chen
5,595,751 A 1/1997 Bezwada
5,597,579 A 1/1997 Bezwada
5,607,687 A 3/1997 Bezwada
5,618,552 A 4/1997 Bezwada
5,620,698 A 4/1997 Bezwada
5,640,978 A 6/1997 Wong
5,645,850 A 7/1997 Bezwada
5,648,088 A 7/1997 Bezwada
5,683,436 A 11/1997 Mendes
5,693,049 A 12/1997 Mersch
5,698,213 A 12/1997 Jamiolkowski
5,700,243 A 12/1997 Narciso, Jr.
5,700,583 A 12/1997 Jamiolkowski
5,707,396 A 1/1998 Benabid ..... A61N 1/326 128/898
5,720,300 A 2/1998 Fagan
5,728,396 A 3/1998 Peery
5,766,234 A 6/1998 Chen
5,769,878 A 6/1998 Kamaei
5,797,868 A 8/1998 Leone
5,800,478 A * 9/1998 Chen et al. ..... 607/88
5,846,220 A 12/1998 Elsberry ..... A61M 25/0068 128/898
5,859,150 A 1/1999 Jamiolkowski
5,910,309 A 6/1999 Ullrich
5,957,960 A * 9/1999 Chen et al. ..... 607/92
5,995,857 A * 11/1999 Toomim et al. ..... 600/322
6,083,919 A 7/2000 Johnson
6,358,272 B1 3/2002 Wilden
6,365,726 B1 4/2002 Ballinger
6,416,531 B2 7/2002 Chen
6,418,344 B1 * 7/2002 Rezai et al. ..... 607/45
6,527,782 B2 * 3/2003 Hogg et al. ..... 606/130
6,537,304 B1 3/2003 Oron
6,551,346 B2 4/2003 Crossley
6,576,000 B2 6/2003 Carrison
6,607,522 B1 8/2003 Hamblin
6,610,713 B2 * 8/2003 Tracey ..... 514/343
6,713,249 B2 3/2004 Hruska
6,736,837 B2 5/2004 Fox
6,921,413 B2 7/2005 Mahadevan-Jansen
7,013,177 B1 3/2006 Whitehurst
7,081,128 B2 7/2006 Hart
7,107,996 B2 9/2006 Ganz
7,288,108 B2 10/2007 DiMauro
7,303,578 B2 12/2007 De Taboada
7,351,253 B2 4/2008 DiMauro
7,354,432 B2 4/2008 Eells et al.
7,435,252 B2 10/2008 Krespi
7,493,171 B1 2/2009 Whitehurst
7,894,905 B2 2/2011 Pless
8,167,920 B2 5/2012 Dimauro
2001/0047195 A1 11/2001 Crossley
2001/0051766 A1 * 12/2001 Gazdzinski ..... 600/309
2002/0016638 A1 2/2002 Mitra
2002/0029071 A1 3/2002 Whitehurst
2002/0087206 A1 7/2002 Hirschberg
2002/0103429 A1 * 8/2002 deCharms ..... 600/410
2002/0122621 A1 9/2002 Li
2002/0198577 A1 12/2002 Jaillet
2003/0097122 A1 5/2003 Ganz
2003/0109906 A1 6/2003 Streeter
2003/0167080 A1 9/2003 Hart et al.
2003/0216797 A1 11/2003 Oron
2003/0236394 A1 * 12/2003 Schwarz et al. ..... 536/23.2
2004/0018557 A1 1/2004 Qu
2004/0030368 A1 2/2004 Kemeny
2004/0049249 A1 * 3/2004 Rubery et al. ..... 607/94
2004/0073278 A1 4/2004 Pachys
2004/0116985 A1 6/2004 Black
2004/0127892 A1 7/2004 Harris
2004/0127961 A1 7/2004 Whitehurst
2004/0219600 A1 11/2004 Williams, III et al.
2005/0070977 A1 3/2005 Molina
2005/0107851 A1 5/2005 Taboada
2005/0107853 A1 5/2005 Krespi
2005/0175658 A1 8/2005 DiMauro
2005/0228291 A1 * 10/2005 Chance ..... 600/476
2005/0279354 A1 12/2005 Deutsch
2006/0004317 A1 1/2006 Mauge
2006/0100679 A1 5/2006 DiMauro
2006/0155348 A1 * 7/2006 deCharms ..... A61N 5/0601 607/89
2006/0161218 A1 7/2006 Danilov
2006/0167531 A1 7/2006 Gertner
2006/0276861 A1 12/2006 Lin
2006/0287695 A1 12/2006 DiMauro
2007/0010859 A1 1/2007 DiMauro
2007/0239235 A1 10/2007 DiMauro
2008/0125836 A1 5/2008 Streeter
2008/0221646 A1 9/2008 DiMauro
2008/0249458 A1 10/2008 Yamasaki
2008/0281305 A1 11/2008 Baynham
2009/0005859 A1 1/2009 Keilman
2009/0054955 A1 2/2009 Kopell
2009/0157141 A1 6/2009 Chiao
2009/0163982 A1 6/2009 deCharms
2009/0222067 A1 9/2009 Toselli
2010/0198316 A1 8/2010 Toselli
2011/0022130 A1 1/2011 Dimauro
2011/0319878 A1 12/2011 DiMauro
2012/0016174 A1 * 1/2012 De Taboada ..... A61N 5/04 600/2

OTHER PUBLICATIONS

Wong-Riley, Light-emitting diode treatment reverses the effect of TTX on cytochrome osidase in neurons, Neuroreport, Oct. 8, 2001, pp. 3033-3037, vol. 12(14).

Yamamoto, Involvement of the olfactory system in learning and memory: a close correlation between the olfactory deficit and the course of Alzheimer's disease?, Yakubutsu Seishin Kodo, 1991, pp. 223-235, vol. 11(4).

Yamamoto, Characteristics of memory dysfunction in olfactory bulbectomized rats and the effects of cholinergic drugs, Behav Brain Res, Feb. 1997, pp. 57-62, vol. 83(1-2).

Volotovskaia, Antioxidant action and therapeutic efficacy of laser irradiation blood in patients with ischemic heart disease, Vopr Kurortol Lech Fiz Kult, May-Jun. 2003, pp. 22-25, vol. 3.

Vladimirov, Molecular and cellular mechanisms of the low intensity laser radiation effect, Biofizika, Mar.-Apr. 2004, pp. 339-350, vol. 49(2).

Sohranji, Local and cortical effects of olfactory bulb lesions on trophic support and cholingeric function and their modulation by estrogen, J Neurobiol, Nov. 2000, pp. 61-74, vol. 45(2).

Tsuboi, Tau pathology in the olfactory bulb correlates with Braak stage, Lewy body pathology and apolipoprotein epsilon4, Neuropathol Appl Neurobiol., Oct. 2003, pp. 503-510, (5).

Powers, Light dosimetry in brain tissue: an in vivo model applicable to photodynamic therapy, Lasers Surg Med., 1986, pp. 318-322, vol. 6(3).

Qiu, Interleukin-6, beta-amyloid peptide and NMDA interactions in rat cortical neurons, J Neuroimmunol, 2003, pp. 51-57, vol. 139(1-2).

Romm, Action of laser radiation on the peroxide chemiluminescence of wound exudate, Biull Eksp Biol Med., Oct. 1986, pp. 426-8, vol. 102(10).

Mann, Alzheimer's disease: an olfactory connection?, Mech Ageing Dev., Jan. 1988, pp. 1-15, vol. 42(1).

Hozumi, Characteristics of changes in cholinergic function and impairment of learning and memory-related behavior induced by olfactory bulbectomy, Behav Brain Res, Jan. 2013, pp. 9-15, vol. 138(1).

Huell, Interleukin-6 is present in early stages of plaque formation and is restricted to the brains of Alzheimer's disease patients, Acta Neuropathol (Berl), 1995, pp. 544-551. vol. 89(6).

(56) References Cited

OTHER PUBLICATIONS

Iakymenko, Regulatory role of low-intensity laser radiation on the status of antioxidant system, Ukr. Biokhim Zh., Jan.-Feb. 2001, pp. 16-23, vol. 73(1).
Ji, Interstitial photoradiation injury of normal brain, Lasers Surg Med, 1992, pp. 425-431, vol. 12(4).
Kamanali, Plasma lipid peroxidation and antioxidant levels in patients with rheumatoid arthritis, Cell Biochem Funct., Jan.-Feb. 2004, pp. 53-57. vol. 22(1).
Klebanov, Effect of low intensity laser light in the red range on macrophages superoxide dismutase activity, Biofizika, May-Jun. 2003, pp. 462-73, vol. 48(3).
Konchugova, Immunodepressive effect of transcerebral lasers, Biull Eksp Biol Med., Apr. 1993, pp. 391-3, vol. 115 (4).
Kovacs, beta-amyloid deposition and neurofibrillary tangle formation in the olfactory bulb in ageing and Alzheimer's disease, Neuropathol Appl Neurobiol., Dec. 1999, pp. 481-91, vol. 25(6).
Kovacs, Olfactory centres in Alzheimer's disease: olfactory bulb is involved in early Braak's stages, Neuroreport., Feb. 2001, pp. 285-8, vol. 12(2).
Chen, Effects of light beam size on fluence distribution and depth of necrosis in superficially applied photodynamic therapy of normal rat brain, Photochem Photobiol., Sep. 1992, pp. 379-84, vol. 56(3).
Cottrell, Mitochondrial enzyme-deficient hippocampal neurons and choroidal cells in AD., Neurology, Jul. 2001, pp. 260-264, vol. 57(2).
Cottrell, The role of cytochrome c oxidase deficient hippocampal neurons in Alzheimer's disease, Neuropathol Appl Neurobiol., Oct. 2002, pp. 390-396, vol. 28(5).
Davies, Axonal loss from the olfactory tracts in Alzheimer's disease, Neurobiol Aging., Jul.-Aug. 1993, pp. 353-357, vol. 14(4).
Del Bo, Reciprocal control of inflammatory cytokines, IL-1 and IL-6, and beta-amyloid production in cultures, Neurosci Lett., Mar. 1995, pp. 70-74, vol. 188(1).
Elias, Hyperthermia from interstitial laser irradiation in normal rat brain, Lasers Surg Med., 1987, pp. 370-375, vol. 7(4).
Giuliani, Very low level laser therapy attenuates edema and pain in experimental models, Int J Tissue React., 2004, pp. 29-37, vol. 26(1-2).
Gorbatenkova, Reactivation of superoxide dismutase by the helium-neon laser irradiation, Biofizika, Jul.-Aug. 1988, pp. 717-719, vol. 33(4).
Gorbatenkova, The red light of the helium-neon laser reactivates superoxide dismutase, Biull Eksp Biol Med., Mar. 1989, pp. 302-305, vol. 107(3).
Haas, Inducible nitric oxide synthase and argininosuccinate synthetase: co-induction in brain tissue of patients with Alzheimer's dementia and following stimulation with beta-amyloid 1-42 in vitro, Neurosci Lett., Apr. 5, 2002, pp. 121-125, vol. 322(2).
Hallam, An investigation of the effect of tacrine and physostigmine on spatial working memory deficits in the olfactory bulbectomised rat, Behav Brain Res., Aug. 31, 2004, pp. 481-486, vol. 153(2).
Balaban, He-Ne laser irradiation of single identified neurons, Lasers Surg Med, 1992, pp. 329-337, vol. 12(3).
Aleksandrova, Increased level of beta-amyloid in the brain of bulbectomized mice, Feb. 2004, pp. 176-180, vol. 69 (2).
Aliev, Atherosclerotic lesions and mitochondria DNA deletions in brain microvessels as a central target for the development of human AD and AD-like pathology in aged transgenic mice, Ann NY Acad Sci., Nov. 2002, pp. 45-64, vol. 977.
Anders, Low power laser irradiation alters the rate of regeneration of the rat facial nerve, Lasers Surg Med., 1993, pp. 72-82, vol. 13(1).
Wollman, In vitro cellular processes sprouting in cortex microexplants of adult rat brains induced by low power laser irradiation, Nuerologic Research, Jul. 1998, pp. 470-472, vol. 20.
Wollman, Low power laser irradiation enhances migration and neurite sprouting of cultured rat embryonal brain cells, Neurological Research, Oct. 1996, pp 467-470, vol. 18.
Snyder, Quantitation of Calcitonin Gene-Related Peptide mRNA and Neuronal Cell Death in Facial Motor Nuclei Following Axotomy and 633 nm Low Power Laser Treatment, Lasers in Surgery and Medicine, 2002, pp. 216-222, vol. 31.
Vladimirov, Photobiological Principles of Therapeutic Applications of Laser Radiation, Biochemistry, 2004, pp. 81-90, vol. 69(1).
Vladimirov, Photoreactivation of Superoxide Dismutase by Intensive Red (Laser) Light, Free Radical Biology & Medicine, 1988, pp. 281-286, vol. 5.
Schindl, Low-Intensity Laser Therapy: A Review, Journal of Investigative Medicine, Sep. 2000, pp. 312-326, vol. 48(5).
Neuman, Narrow-band red light phototherapy in perennial allergic rhinitis and nasal polyposis, Annals of Allergy, Asthma, & Immunology, Apr. 1997, pp. 399-406, vol. 78.
Mochizuki-Oda, Effects of near-infra-red laser irradiation on adenosine triphosphate and adenosine diphosphate contents of rat brain tissue, Neuroscience Letters, 2002, pp. 207-210, vol. 323.
Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Lasers in Surgery and Medicine, 2002, pp. 283-288, vol. 31.
Hebeda, Light Propagation in the Brain Depends on Nerve Fiber Orientation Experimental Study, Neurosurgery, Oct. 1994, pp. 1992-1998, vol. 35(4).
Byrnes, Light Promotes Regeneration and Functional Recovery and Alters the Immune Response After Spinal Cord Injury, Lasers in Surgery and Medicine, 2005, pp. 1-15, vol. 9999.
Anders, Phototherapy promotes regeneration and functional recovery of injured peripheral nerve, Neurological Research, Mar. 2004, pp. 233-239, vol. 26.
Aliev, Mitochondria and vascular lesions as a central target for the development of Alzheimer's disease and Alzheimer's like pathology in transgenic mice; Neurological Research, Sep. 2003 pp. 665-674, vol. 25(6).
Cho, Effect of low-level laser therapy on osteoarthroplasty in rabbut, in Vivo, 2004, Sep.-Oct. pp. 585-591, vol. 18(5).
Aliev, Mitochondria and Vascular Resigns As a Central Target for the Development of Alzheimer's Disease and Alzheimer's Disease-like Pathology in Transgenic Mice, Neurol. Res., 2003, Sep. pp. 665-674, vol. 25(6)
Balasingam, Attenuation of Astroglial Reactivity by Interleukin-10, J. Neuroscience, May 1, 1996, pp. 2945-2955, vol. 16(9).
Brennan, Interleukin 10 and Arthritis, Rheumatology, 1999, pp. 293-297, vol. 38.
Brodie, Differential Effects of Th1 and Th2 Derived Cytokines on NGF Synthesis Mouse Astrocytes, FEBS Lett., 1996, pp. 117-120, vol. 394(2), Federation of European Biochemical Societies.
Brown et al., Gelatin/Chondroitin 6-Sulfate Microspheres for the Delivery of Therapeutic Proteins to the Joint, Arthritis. Rheum. Dec. 1998; pp. 2185-2195, vol. 41(12), American College of Rheumatology.
Burkoth, A Review of Photocrosslinked Polyanhydrides: in situ Forming Degradable Networks, Biomaterials, 2000, pp. 2395-2404. vol. 2, Elsevier Science Ltd.
Dugan, Fullerene-based Antioxidants and Neurodegenerative Disorders, Parkin. Relat. Disord., Jul. 2001, pp. 243-246 , vol. 7(3).
Ebadi, Peroxynitrite and Mitochondrial Dysfunction in the Pathogenesis of Parkinson's disease, Antioxidants & Redox Signaling, 2003, pp. 319-335, vol. 5(3).
Gonzalez, Protection Against MPP+ Neurotoxicity in Cerebellar Granule Cells by Antioxidants, Cell Biology Int'l, 2004, pp. 373-380, vol. 28.
Hart, Comparison of the Suppressive Effects of Interleukin-10 and Interleukin-4 on Synovial Fluid Macrophages and Blood Monocytes From Patients With Inflammatory Arthritis, Immunology, Apr. 1995, pp. 536-542, vol. 84(4).
Itoh, Defects of Cytochrome c Oxidase in the Substantia Nigra of Parkinson's Disease: An Immunohistochemical and Morphometric Study., Mov. Disord., Jan. 1997, pp. 9-16, vol. 12(1).
Johanson, Choroid Plexus Recovery After Transient Forebrain Ischemia: Role of the Growth Factors and Other Repair Mechanisms, Cell. Mol. Neurobiol., 2000, pp. 197-216, vol. 20(2).

(56) References Cited

OTHER PUBLICATIONS

Kang, CD11b+ Macrophages That Infiltrate Human Epidermis After in Vivo Ultraviolet Exposure Potently Produce IL-10 and Represent the Major Secretory Source of Epidermal IL-10 protein1, J. Immunol., 1994, pp. 5256-5264, vol. 153, The American Association of Immunologists.
Karu, Suppression of Human Blood Chemiluminescence by Diode Laser Irradiation at Wavelengths 660, 820, 880 or 950 nm., Laser Ther. 1993, pp. 103-109, vol. 5.
Kelly, The Anti-inflammatory Cytokin, Interleukin (IL)-10, Blocks the Inhibitory Effect of IL-1B on Long Term Potentiation, J. Biol. Chem., 2001, pp. 45564-45572, vol. 276(49), JBC Papers in Press.
Knoblach, Interleukin-10 Improves Outcome and Alters Proinflammatory Cytokins Expression After Experimental Traumatic Brain Injury, Exp. Neuro., 1998, pp. 143-151, vol. 153, Academic Press.
Mark et al., "Hydrogels", Concise Encyclopedia of Polymer Science and Engineering, 1990, pp. 458-459, Wiley and Sons.
Nakao, Overexpressing Cu/Zn Superoxide Dismutase Enhances Survival of Transplanted Neurons in a Rat Model of Parkinson's Disease, Nat. Med. Mar. 1995, pp. 226-231, vol. (3).
Nowak, The Effect of Superpulsed Carbon Dioxide Laser Energy on Keloid and Normal Dermal Fibroblast Secretion of Growth Factors: A Serum-Free Study, Plast. Reconstr. Surg., 2000, pp. 2039-2048, vol. 105(6).
Ostrakhovich, Active Forms of Oxygen and Nitrogen in Blood Cells of Patients With Rheumatoid Arthritis: Effect of Laser Therapy, Vestn Ross Akad Med Nauk. 2001, pp. 23-27, vol. 5.
Prehn, Protective Effect of Transforming Growth Factor-B1 on B-Amyloid Neurotoxicity in Rat Hippocampal Neurons, Mol. Pharm. Feb. 1996, pp. 319-328, vol. 49(2), The American Society for Pharmacology and Experimental Therapeutics.
Ren, Transforming Growth Factors-B Protect Primary Rat Hippocampal Neuronal Cultures From Degeneration Induced by B-amyloid Peptide, Brain. Res., Sep. 2, 1996, pp. 16-24, vol. 732 (1-2), Elsevier Science B.V.
Rivas, Systemic Suppression of Delayed-Type Hypersensitivity by Supernatants From UV-Irradiated Keratinocytes, J. Immun, Dec. 15, 1992, pp. 3865-3871, vol. 149(12), The American Association Immunologists.
Sawada, Interleukin-10 Inhibits Both Production of Cytokines and Expressoin of Cytokine Receptors in Microglia, J. Neurochemistry, 1999, pp. 1466-1471, vol. 72, Lippincott Williams & Wilkins.
Schmitt, Exposure to Ultraviolet Radiation Causes Dendritic Cells/Macrophages to Secrete Immune-Suppressive IL-12p40 Homodimers, J. Immunology, 2000, pp. 3162-3167, vol. 165.
Serot, A Cytokine Cascade Including Prostaglandin E2,IL-4 and IL-10 Is Responsible for UV-Induced Systemic Immune Suppression, J. Neuroimmunology, 2000, pp. 115-119, vol. 104.
Shreedhar, A Cytokine Cascade Including Prostaglandin E2, IL-4 and IL-10 Is Responsible for UV-Induced Systemic Immune Suppression, J. Immunol., 1998, pp. 3783-3789, vol. 160, The American Association of Immunologists.
Strle, Interleukin-10 in the Brain, Cult. Rev. Immunology, 2001, pp. 427-449, vol. 21(5).
Strle, IL-10 Promotes Survival of Microglia Without Activating Akt, J. Neuroimmunology, Jan. 2002; pp. 9-19, vol. 122(1-2).
Stutzmann, GaN-based Heterostructures Sensor Applications, Diamond and Related Materials, 2002, pp. 886-891, vol. 11, Elsevier Science B.V.
Sutton, Amyloid-B peptide induced inflammatory reaction is mediated by the cytokines tumor necrosis factor and interleukin-1, J. Submicrose.Cytol. Pathol., 1999, pp. 313-323, vol. 31(3), Elsevier Science B.V.
Szczepanik, II-4, IL-10 and IL-13 Modulate AB)1-42)-Induced Cytokine and Chemokine Production in Primary Murine Microglia and a Human Monocyle Cell Line, J. Neuroimmunology, 2001, pp. 49-62, vol. 113.
Town, Reduced Th1 and Enhanced Th2 Immunity with Alzheimer's B-amyloid 1-42, J. Neuroimmunol., (2002), pp. 49-89, vol. 132, Elsevier Science B.V.
Vitreshchak, Laser Modification of the Blood in Vitro and in Vivo in Patients with Parkinson's Disease Bull. Exp. Biol. Med., May 2003, 430-432, vol. 135(5).
Vladimirov, Photobiological Principles of Therapeutic Application of Laser Radiation, Biochemistry, 2004, pp. 103-113, vol. 69(1), Moscow.
Walicke, Purification of a Human Red Blood Cell Protein Supporting the Survival of Cultured CNS Neurons and its Identification as Catalase, J. Neuroscience, Apr. 1986, pp. 1114-1121, vol. 6(4).
Wong-Riley, Photobiomodulation Directly Benefits Primary Neurons Functionally Inactivated by Toxins: Role of Cytochrome C Oxidase, J. Biol. Chem., Feb. 11, 2005, pp. 4761-4771, vol. 280(6), Epub Nov. 22, 2004.
Bachis, Interleukin-10 Prevents Glutamate-Mediated Cerebellar Granule Cell Death by Blocking Caspase-3-Like Activity, J. Neuroscience, May 1, 2001, pp. 3104-3112, 21(9).
Grilli, Interleukin-10 modulates neuronal threshold of vulnerability to ischaemic damage, Eur. J. Neuroscience, Jul. 2000, pp. 2265-2272, 12(7).
Lio, Interleukin-10 promoter polymorphism in sporadic Alzheimer's disease, Genes Immun., 2003, pp. 234-238, vol. 4.
Schmidt, Evaluation of Photodynamic Therapy Near Functional Brain Tissue in Patients With Recurrent Brain Tumors, Journal of Neuro-oncology, 2004, pp. 201-207, vol. 67, Kluwer Academic Publishers, The Netherlands.
Adam, "A Clinical Trial of Hypertonic Saline Nalas Spray in Subjects With the Common Cold or Rhinosinusitis", Archives of Family Medicine, 1998, vol. 7, pp. 39-43, American Medical Association.
Allcock, "Polyphosphazenes", The Encyclopedia of Polymer Science, 1988, pp. 31-41, vol. 13, Wiley Intersciences, John Wiley & Sons.
Bhardwaj, "Hypertonic Saline Worsens Infarct Volume After Transient Focal Ischemia in Rats Editorial Comment", Stroke, 2000, vol. 31, pp. 1694-1701, American Heart Association.
Cohn and Younes, "Biodegradable PEO/PLA block copolymers", Journal of Biomaterials Research, 1988, pp. 993-1009, vol. 22, John Wiley and Sons.
Cohn, Polymer Preprints, Biomaterials Research Laboratory, (ACS Division of Polymer Chemistry), 1989, p. 498, vol. 30(1),(e.g. PEO/PLA).
Eels, Mitochondrial signal transduction in accellerated wound and retinal healing by near-infrared light therapy, Mitochondrion, 2004, pp. 559-567, vol. 4, Elsevier B.V.
Heller, "Development of Poly(Ortho Esters)", Handbook of Biodegradable Polymers, 1997, pp. 99-118, Hardwood Academic Press.
Kemnitzer and Kohn, "Degradable polymers derived from the amino acid L-Tyrosine", the Handbook of Biodegradable Polymers, 1997, pp. 251-272 Hardwood Academic Press.
Koh, "Development of cerebrospinal fluid absorption sites in the pig and rat" Anat. Embryol (BerI), Mar. 10, 2006 (e-pub).
Koh, "Integration of the subarachnoid space and lymphatics: Is it time to embrace a new concept of cerebrospinal fluid absorption?", Cerebrospinal Fluid Research 2005, 2:6, 11 pages.
Louin, "Selective inhibition of inducible nitric oxide synthase reduces neurological deficit but not cerebral edema following traumatic brain injury", Neuropharmacology, Feb. 2006, 50(2) 182-90, Elsevier.
Nagra, "Quantification of cerebrospinal fluid transport across the cribriform plate into lymphatics of rats", Am. /. Physiol. Regul. Integr. Compo Physiol. Jun. 22, 2006 (e-pub).
Schwarz, "Effects of hypertonic (10%) saline in patients with raised intracranial pressure after stroke" Stroke, 2002, 33, pp. 136-140, American Heart Association.
Shirasawa, "Physiological roles of endogenous nitric oxide in lymphatic pump activity of rat mesentery in vivo" Am. J. Physiol. Gastrointest. Liver Physiol., 2000, pp. G551-G556, vol. 278, The American Physiological Society.
Unterberg, "Edema and Brain Trauma", Neuroscience, 2004, 1021-1029, vol. 129, Elsevier Ltd.
Vandorpe, "Biodegradable Polyphosphazenes for Biomedical Applications", Handbook of Biodegradable Polymers, 1997, pp. 161-182, Hardwood Academic Press.

(56) References Cited

OTHER PUBLICATIONS

Vink, "Novel therapies in development for the treatment of traumatic brain injury", Exp. Op. Invest. Drugs, Oct. 2002, pp. 1375-1386, vol. 11(1), Ashley Publications Ltd.
Vink, "Recent advances in the development of multifactorial therapies for the treatment of traumatic brain injury", Exp. Op. Invest. Drugs, 2004, pp. 1263-1274—vol. 13(10), Ashley Publications Ltd.
Von Der Weid, "Nitric oxide decreases pacemaker activity in lymphatic vessels of guinea pig messentry", Am. J. Physiol. Heart Circ. Physiol., Jun. 2001: 280(6)H2707-16, The American Physiology Society.
Zawieja, "Inhibition of the active lymph pump in rat mesenteric lymphatics by hydrogen peroxide", Lymphology, Sep. 1993, 26(3) pp. 135-142—abstract.
Angell-Petersen, "Determination of fluence rate and temperature distributions in the rat brain; implications for photodynamic therapy". J. Biomed Optics, 12(1),014003-1-9 (Jan.-Feb. 2007) Abstract.
Bernier, "Characterization of the subventricular zone of the adult human brain: evidence for the involvement of Bc1-2", Neurosci. Res. 37 (2000) 67-78.
Blair, "The Anterior Thalamic Head-Direction Signal Is Abolished by Bilateral But Not Unilateral Lesions of the Lateral Mammillary Nucleus", J. Neuroscience, Aug. 1, 1999, 19(15) 6673-83.
Byrnes, "Light promotes regeneration and functional recovery and alters the immune response after spinal cord injury", Lasers Surgery Medicine, Mar. 2005, 36(3) 171-185 Abstract.
Byrnes, "Low power laser irradiation alters gene expression of olfactory ensheathing cells in vitro", Lasers Surg Med., Aug. 2005; 37(2):161-71 Abstract.
Damier, "The substantia nigra of the human brain II. Patterns of loss of dopamine-containing neurons in Parkinson's disease", Brain 1999, Aug. 122(Pt. 8; 1437-48.
Duprez, "MR Imaging Findings of Cortical Blindness Following Cerebral Angiography: Is This Entity Related to Posterior Reversible Leukoencephalopathy?", Am. J. Neuroradiology 26:195-198, Jan. 2005.
Farin, "Endoscopic third ventriculostomy", Clin. Neurosci. Aug.; 13(7);2006 , 763-70.
Kleiner-Fisman, "Subthalamic Nucleus Deep Brain Stimulation: Summary and Meta-Analysis of Outcomes", Mov. Disord., Jun. 21, 2006, Suppl. 14 S290-304.
Nait-Oumesmar, "Activation of the subventricular zone in multiple sclerosis: Evidence for early glial progenitors", Proc Natl. Acad Sci USA. Mar. 15, 2007 13;104(11):4694-9.
Oron, "Ga-As (808 nm) laser irradiation enhances ATP production in human neuronal cells in culture", Photomed. Laser Surg., Jun. 2007; 25(3) 180-2.
Oron, "Low-Level Laser Therapy Applied Transcranially to Rats After Induction of Stroke Significantly Reduces Long-Term Neurological Deficits", Stroke. 2006;37:2620-2624; originally published online Aug. 31, 2006.
Shan, "Enhanced De Novo Neurogenesis and Dopaminergic Neurogenesis in the Substantia Nigra of 1-Methyl-4-phenyl-1,2,3,6-Tetrahydropyridine-Induced Parkinson's Disease-Like Mice", Stem Cells, 2006, 24:1280-7.
Stefani, "Bilateral deep brain stimulation of the pedunculopontine and subthalamic nuclei in severe Parkinson's disease", Brain, 2007, 130(6), 1596-1607.
Vann, "The Mammillary Bodies: Two Memory Systems in One?", Nature Reviews: Neuroscience, vol. 5 Jan. 2004, 35-44.
Victor, "The irrelevance of mammillary body lesions in the causation of the Korsakoff amnesic state.", Int'l J. Neurol., 1987-8, 21-22, 51-7.
Welter, "Effects of Hugh-Frequency Stimulation on Subthalamic Neuronal Activity in Parkinsonian Patients", Arch. Neurol. 2004: 61:89-96.
Freundlieb, "Dopaminergic Substantia Nigra Neurons Project Topographically Organized to the Subventricular Zone and Stimulate Precursor Cell Proliferation in Aged Primates", The Journal of Neuroscience, Feb. 22, 2006, vol. 26(8), pp. 2321-2325.

* cited by examiner

AMENDED FIG. 6
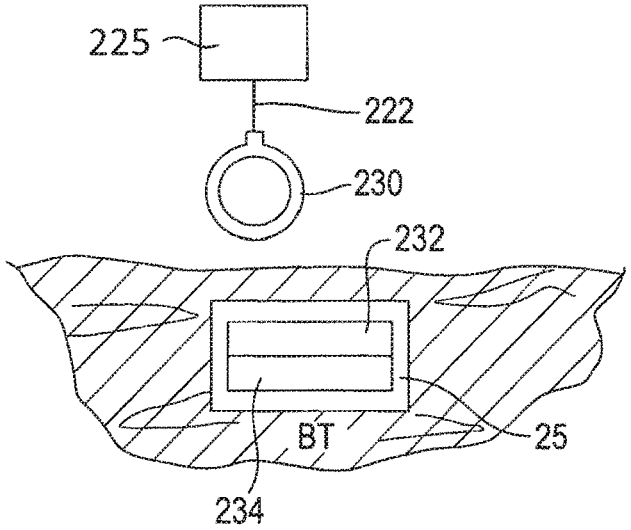
FIG. 7
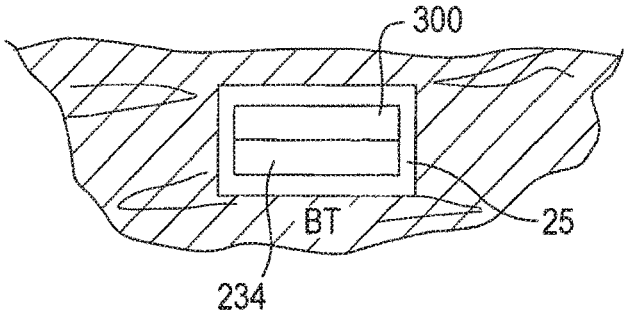

FIG. 10A
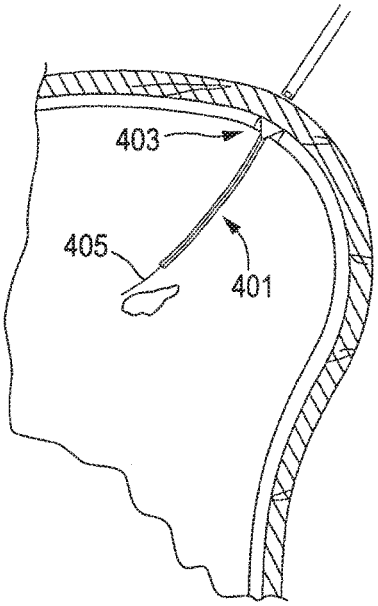
AMENDED FIG. 10B
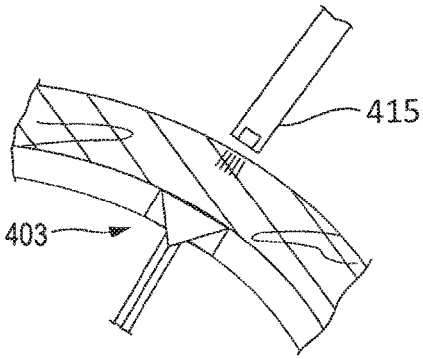

LIGHT-BASED IMPLANTS FOR TREATING ALZHEIMER'S DISEASE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CONTINUING DATA

This patent application claims priority from U.S. Provisional Patent Application No. 60/661,629 field on Mar. 14, 2005 entitled "Light-Based Implants for Treating Alzheimer's Disease", the disclosures of which are hereby incorporated by reference in their entirety.

BACKGROUND OF THE INVENTION

In Alzheimer's Disease (AD), the cleavage of beta amyloid protein precursor from the intracellular membrane often produces a protein AB-42 which is incompletely removed by normal clearance processes. Over time, this protein is deposited as a beta amyloid protein Aβ plaque within brain tissue, leading to the local destruction of neurons. The Aβ plaque deposition is also believed to provoke an inflammatory response by microglia and macrophages, which recognize the plaque as a foreign body. These cells are believed to respond to the plaque deposition by releasing pro-inflammatory cytokines and reactive oxygen species (ROS). Although the inflammatory response may be provoked in an effort to clear the brain tissue of the detrimental plaque, it is now believed that this inflammation also injures local neuronal tissue, thereby exacerbating AD.

Because of the role played in AD by inflammation, anti-inflammatory compounds have been identified as candidates for treating Alzheimer's Disease. However, the delivery of these compounds has generally been through an oral route, and the systemic side effects associated with long term use of these compounds are often undesirable.

Some investigators have proposed implanting an effective amount of NGF in a sustained release device for treating Alzheimer's Disease. However, NGF simply helps restore damaged neurons—it does little to stop the damage from occurring.

SUMMARY OF THE INVENTION

The present inventor has developed methods for treating or preventing Alzheimer's Disease (AD) exploiting the characteristics of a particular cytokine, interleukin-10 (IL-10).

It is believed that IL-10 possesses a number of features that make it an attractive therapeutic agent for treating neuropathic diseases, such as Alzheimer's Disease. These include the inhibition of cytokine synthesis and the downregulation of antigen-presenting cell function:

According to Brennan, Rheumatology 1999, 38, 293-7, IL-10 can induce the production of cytokine inhibitors, including the IL-1 receptor antagonist (IL-1ra) and the release of both soluble TNF receptors p55 and p75 in monocytes. Because of this utility, Brennan chartacterizes IL-10 as a 'macrophage deactivating factor'.

According to Hart, Immunology, 1995, April 84 (4) 536-42, IL-10 and Il-4 have the capacity to downregulate both pro-inflammatory molecules TNF-α and IL-1β. Szczepanik, J. Neuroimmunology, 113(2001, 49-62 reports that IL-10 was found to suppress all Aβ-induced and LPS-induced inflammatory proteins measured, including Il-1a, IL-1B, IL-6, TNF-a and MCP-1. Kelly, J. Biol. Chem. 276(49) 45564-72, reports that IL-10 antagonizes IL-1β effects in the hippocampus. According to Knoblach, Exp. Neuro., 153, (1998) 143-51, at the level of the hippocampus, recovery following traumatic brain injury was improved by treatment with IL-10, and this effect was associated with a decreased concentration of IL-1β in the hippocampus. Sawada, J. Neurochemistry, 72, 1466-71, 1999, reported that IL-10 is a unique and potent inhibitor in the CNS cytokine network and inhibits both the production of cytokines and expression of cytokine receptors in microglia. Balsasingam, J. Neuroscience, May 1, 1996, 16(9), 2945-55, reports that astroglial activity following brain injury is attenuated by IL-10 and concluded that Il-10 is a potent inhibitor of cytokine synthesis by macrophages and microglia.

As noted above, one of the key lynchpins in the initiation of AD is the deposition of Aβ. It is believed that increased levels of IL-1 lead to increased Ab deposition. According to Sutton, J. Submicrosc. Cytol. Pathol., 31(3), 313-23, 1999, Il-1 derived from microglia upregulates expression and processing of Aβ precursors proteins, thus favoring Aβ deposits which may in turn through feedback loops activate microglia to further IL-1 production. In addition, it has been reported that pretreatment with IL-1ra administered intracerebroventricularly_resulted in a reduction in the extent and density of Aβ precursor protein. Therefore, since Il-10 has been demonstrated to upregulate IL-1ra and downregulate Il-1β, and Il-1 promoted Aβ deposition, it appears reasonable to conclude that IL-10 should therefore antagonize Aβ deposition.

Town, J. Neuroimmunol., 132 (2002) 49-59 examined the status of Th1 and Th2 cells in mice after immunization with beta-amyloid. Town reported that interferon-gamma was markedly reduced, that IL-10 was increased in blood plasma from these mice, and that these effects were associated with dramatically mitigated amyloid-beta deposition after immunization with beta-amyloid.

According to Brodie, FEBS Lett., 1996, Sept. 30, 394(2), 117-20, when IL-10 contacts astrocytes, it induces the production of nerve growth factor (NGF)—another very important biologic in AD therapy. Therefore, IL-10 may not only inhibit inflammation associated with AD, it may also enhance nerve repair.

Strle, J. Neuroimmunology, 2002 January; 122(1-2):9-19 reports that IL-10 promotes the survival of microglia without activating Akt, with as little as 0.1 ng/ml of Il-10 significantly reducing DNA fragmentation. Grilli, Eur. J. Neuroscience, 12(7), July 2000, 2265 reports that 0.1-100 ng/ml IL-10 exerted a concentration dependent prevention of neuronal damage induced by excitotoxicity, and concluded that there is a potential neuroprotective role for Il-10 against cerebral ischemia. Bachis, J. Neuroscience, 21(9), May 1, 2001, 3104-12, suggestes that the neuroprotective properties of Il-10 may rely on its ability to block the activity of proapoptitic proteins. Therefore, IL-10 may have a neuroprotective role as well.

Lio, Genes Immun., 2003, April 4(3), 234-8 reports that subnormal levels of IL-10 are found in patients with AD versus controls. Since the inflammatory cascade described above may be due in part to a low level of IL-10 in the patient's CSF, it is believed that enhancing the level of IL-10 in an AD brain tissue will have a therapeutic effect by providing increased antagonism to inflammation.

Strle, Crit. Rev. Immunology; 2001, Vol. 21 Issue 5, concludes that the multiple functions of IL-10 in the brain will create new and interesting vistas that will promote a better understanding of neurodegenerative diseases which could lead to the development of innovative approaches for the use of anti-inflammatory cytokines in major debilitating diseases of the central nervous system.

The concept of administering UVB light to therapeutically treat an auto-immune disease by producing autologous IL-10 is disclosed in U.S. Pat. No. 5,910,309 (Ullrich), the disclosure which is hereby incorporated by reference in its entirety. Shreedhar, J. Immunol., 1998, 160, 3783-9, suggests that UV irradiation of keratinocytes activates a cytokine cascade within the cells of the skin that involves macrophage recruitment as follows:

$PGE_2 \rightarrow$IL-4$\rightarrow$Il-10.

Although Ullrich appreciates the benefits of IL-10, the methods of providing IL-10 disclosed by Ullrich generally concern full body irradiation producing systemic increases in IL-10. Since IL-10 has a potent immunosuppressive effect, the patient receiving such treatment would be at risk of undesired side effect of having a suppressed immune system, including an increased susceptibility towards infection.

The present inventors have noted that the autologous cells that produce IL-10 when activated by UV-B radiation (macrophages, microglia, lymphocytes and astrocytes) are the same cells that participate in the inflammatory response characteristic of Alzheimer's Disease. Therefore, it appears that a great concentration of cells capable producing of IL-10 reside precisely within the region of undesired inflammation. Therefore, it is believed that Alzheimer's Disease may be effectively treated by irradiating the inflamed region with UV-B light, thereby de-activating the pro-inflammatory ($Th_1$) cells in that region that are emitting pro-inflammatory cytokines and activating the IL-10-emitting ($Th_2$) cells.

Therefore, without wishing to be tied to a theory, it is further believed that UVB light may also be effective in activating the Th2 pathway in local cells and inactivating the Th1 pathway. Because the Th2 pathway is considered to be anti-inflammatory while the Th1 pathway is considered to be pro-inflammatory, the effect of UVB light may be that of immunosuppression. This quality may help attenuate AD.

Also without wishing to be tied to a theory, it is further believed that UVB light may also be effective in causing the release of calcitonin gene related peptide (CGRP), which in turn may cause mast cells to degranulate and release IL-10, thereby attenuating AD.

Accordingly, in some embodiments of the present invention, there is provided a method of treating or preventing Alzheimer's disease, comprising the steps of:

a) providing an implant having a UV light source,
b) positioning the implant within or adjacent to brain tissue, and
c) activating the light source to irradiate the brain tissue with an amount of UV light sufficient to activate cells therein to produce IL-10.

DESCRIPTION OF THE FIGURES

FIG. 6 is a representation of the device of the present invention powered by an internal light source.

FIGS. 7 and 8 are representations of devices of the present invention wherein the internal light source is powder by an internal battery.

FIGS. 10A-10B are cross-sections of a fiber optic implant of the present invention implanted within the brain of a patient having Alzheimer's Disease.

DETAILED DESCRIPTION OF THE INVENTION

Figure 1:
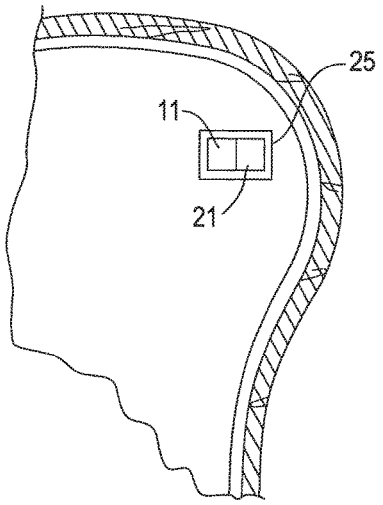
FIG. 1 is a representation of the device of the present invention implanted into a brain.

Now referring to FIG. 1, there is provided an implant for treating Alzheimer's disease comprising:

a) a UV-B Light emitting diode (LED) 11, and
b) an antenna 21 in electrical connection with the LED.

In use, the surgeon implants the device into the brain of the patient so that the device is adjacent to a portion of the brain which is inflamed. The IL-10 produced by the implant will then affect the area of inflammation. However, investigators have noted systemic immunosuprresive effects in animals subject to whole body UV irradiation, and have hypothesized that the mobility of the irradiated macrophages allows them to migrate to vast regions of tissue. See Kang, J. Immunol., 1994, 153, 5256. Accordingly, it is possible that irradiated cells (such as microglia and macrophages) in one portion of the brain may be sufficient to arrest inflammation over a much larger region of the brain. Therefore, it is possible that the implant need not be immediately adjacent the inflamed tissue, but rather may be placed at a more convenient spot for the surgeon, such as near the skull.

In order to protect the active elements of the device from the CSF, in some embodiments, and again referring to FIG. 1, the UV LED is encased in a casing 25. This casing both protects the LED components from the CSF, and also prevents the LED components from eliciting a violent immune reaction In some embodiments, the casing is made of a UV transparent material. The UV transparent material may be placed adjacent the LED component so that UV light may be easily transmitted therethrough. In some embodiments, the UV transparent casing is selected from the group consisting of silica, alumina and sapphire. In some embodiments, the light transmissible material is selected from the group consisting of a ceramic and a polymer. Suitable UV-transmissible ceramics include alumina, silica, CaF, titania and single crystal-sapphire. Suitable light transmissible polymers are preferably selected from the group consisting of polypropylene and polyesters.

In some embodiments, it may be desirable to locate the light emitting portion of the implant at a location separate from the LED, and provide a light communication means between the two sites. The light communication means may include any of a fiber optic cable, a wave guide, a hollow tube, a liquid filled tube, and a light pipe.

Figure 2:
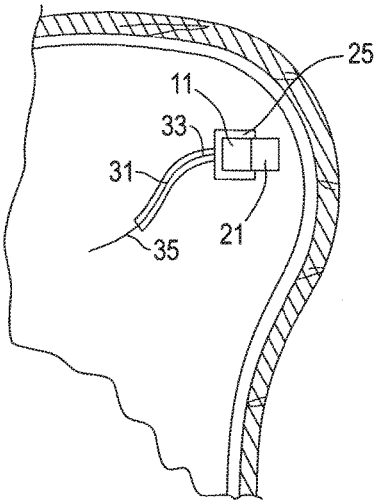
FIG. 2 is a representation of a device of present invention having a fiber optic cable.

Now referring to FIG. 2, there is provided an implant 1 for treating Alzheimer's disease comprising:

a) a UV-B Light emitting diode (LED) 11,
b) an antenna 21 in electrical connection with the LED, and c) a fiber optic cable 31 adapted to transmit UV-B light, the cable having a proximal end 33 connected to the LED an and a distal end portion 35.

Such a configuration would allow a fiber optic to be located deep within the patient, or in or near critical organs or tissues, and yet have the light source and associated components in a less sensitive region. This configuration allows easier access to the light/controller should the need arise for service or maintenance, and also allow for more efficient transdermal energy transmission. Moreover, by using a hollow tube with reflective internal surfaces, light and therapeutic fluids could be delivered to the implanted device. The light source/controller implanted near the patient's skull could also be a simple, hollow chamber made to facilitate the percutaneous access described above. The advantages and benefits of this system include:

a) further removal from the deep site of the functional implant, thereby reducing risk of contamination of the deeper site by percutaneous access;

b) easier precutaneous access by being closer to the skin surface and having a larger surface area or target to access with the needle;

c) a larger volume could hold more therapeutic fluid to provide a longer duration of activity; and d) a central reservoir could provide therapy to multiple implants throughout the body.

In use, the surgeon implants the device into the brain of the patient so that the antenna is adjacent the cranium bone and the distal end of the fiber optic cable is adjacent to a more central inflamed region of the brain.

In Alzheimer's disease, it is believed that plaque deposition and its attendant inflammation begins within the hippocampus portion of the brain. Therefore, in some embodiments, the distal end portion of the fiber optic cable is located adjacent to the hippocampus HC.

Since it is the UV light that converts the pro-inflamatory cells to an anti-inflammatory status, it is desirable to design the device so that the UV light is emitted only in regions of inflammation. Since the inflamed regions of an Alzheimer's brain are often located in the central regions of the brain, in some embodiments, the proximal end portion of the fiber optic cable is provided with a cladding layer 41 of reflective material to insure that UV light does not escape the cable into uninflamed regions of brain tissue.

Figure 3:
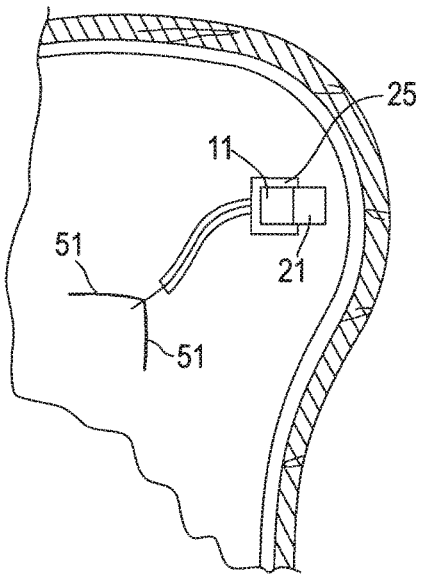
FIG. 3 is a representation of a device of present invention having a fiber optic cable having a plurality of tynes.

Because UV-B light typically can penetrate tissue to a depth of only about 1 mm, it may be advantageous to increase the area of the UV-emitting surface in order to affect more inflamed tissue. Accordingly, in some embodiments, the distal end portion of the fiber optic cable includes a plurality of fiber optic tynes 51 extending from the cable (as shown in FIG. 3). Since each of these tynes transmits UV-B light into brain tissue, the provision of tynes increases the volume of brain tissue that can be converted to an anti-inflammatory status.

In some embodiments, the tynes located at distal end portion of the fiber optic cable are placed around the hippocampus HC.

Figure 4:
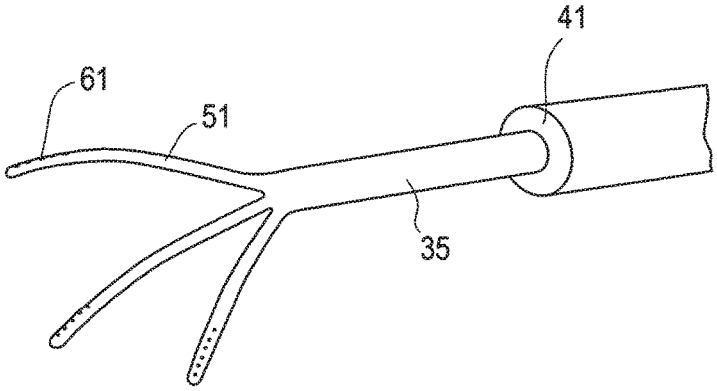
FIG. 4 is a representation of a device of present invention having a fiber optic cable having an etched distal portion.

Shreedhar, J. Immunol., 1998, 160, 3783-9 has reported that UV-induced IL-10 production is enhanced in the presence of IgG. Accordingly, in some embodiments, a distal portion of the fiber optic cable has an etched surface 61 (as shown in FIG. 4). Without wishing to be tied to a theory, it is believed that the etched portion will cause IgG to bind thereto (see, Reinecke, U.S. Pat. No. 6,713,246). The presence of the IgG in the UV-irradiated zone of tissue will increase the rate of Il-10 production therein. Etched glass can be produced in a manner substantially similar to that described in U.S. Pat. No. 6,713,246, the specification of which is incorporated by reference in its entirety.

In some embodiments, the UV light source is situated to irradiate adjacent tissue with between about 0.02 J/cm$^2$ and 20 J/cm$^2$ energy. Without wishing to be tied to a theory, it is believed that light transmission in this energy range will be sufficient to activate the macrophages and astrocytes of most brain tissue. Shreedhar, J. Immunol., 1998, 160, 3783-9 has reported using a light dose of 0.02 J/cm$^2$ in order to activate keratinocytes to produce IL-10. Schmitt, J. Immunology, 2000, 165:3162-7 has reported using a dose of 1.5 J/cm$^2$. Rivas, J. Immun, 149, 12, 1992, 3865-71 has reported using a dose of 0.02 J/cm$^2$. Therefore, it is believed that irradiating inflamed brain tissue with at least about 0.02 J/cm$^2$ of UV radiation will induce the macrophages and microglia therein to produce and emit Il-10. In some embodiments, the light source is situated to produce an energy intensity at the cell surface of between 0.1 watts/cm$^2$ and 10 watts/cm$^2$. In some embodiments, the light source is situated to produce about 1 milliwatt/cm$^2$. This latter value has been reported by Ullrich to effectively irradiate a cell surface in an amount sufficient to produce IL-10.

As noted above, in some embodiments, the tynes of the fiber optic are laid adjacent to the hippocampus. Because the hippocampus has a dimension that is often less than about 3 cm, the surface area of the hippocampus is typically no more than about 30 $cm_2$. Accordingly, only about 0.6-60 J are required in order to activate the cells within the hippocampus. Therefore, a 0.5 W emission would require a radiative duration of about 3 second to 120 seconds to produce 0.6-60 J.

Figure 5:
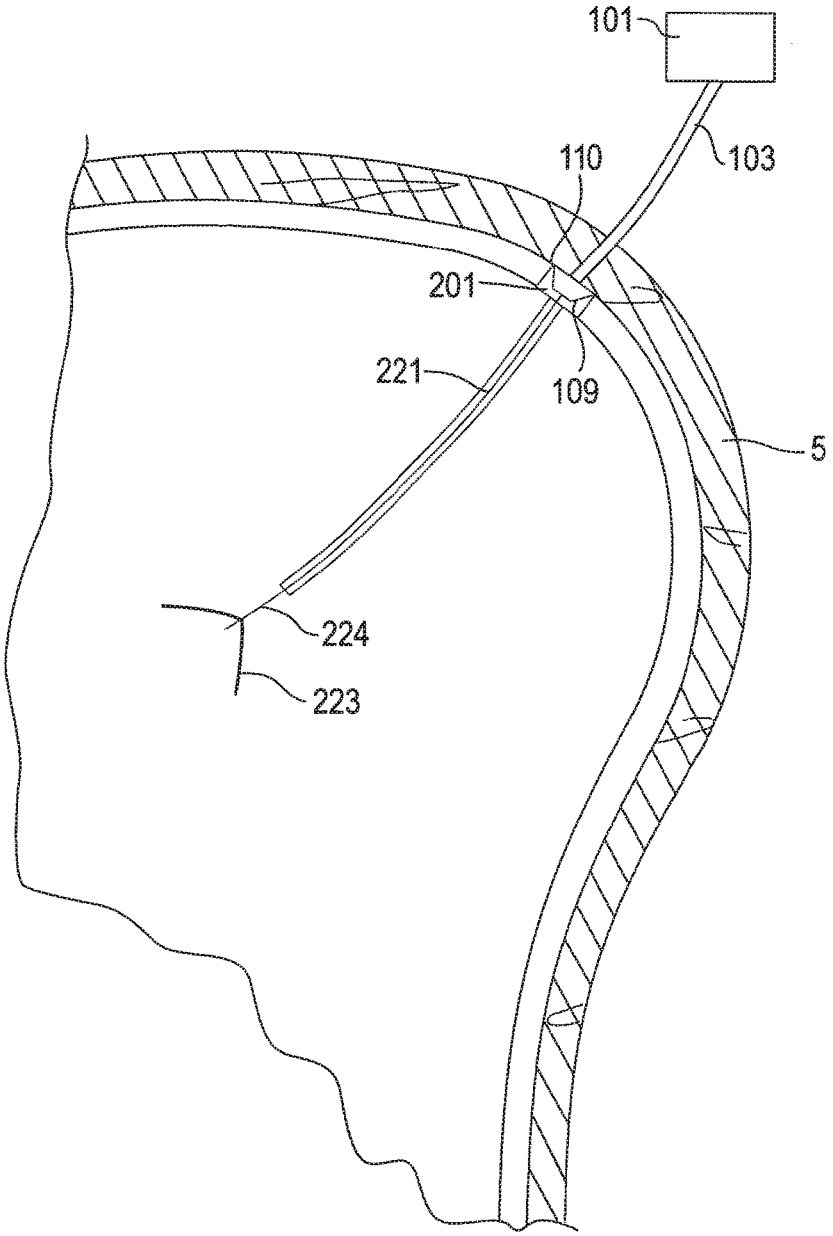
FIG. 5 is a representation of the device of the present invention powered by an external light source.

Now referring to FIG. 5, there is provided a first exemplary implant having an external light source. The externally based-control device has a light source 101 for generating light within the device. The light generated by this source is transmitted through fiber optic cable 103 through the patient's skin [S] *5* to an internally-based light port 109 provided on the proximal surface 110 of the implant 201. The light port is adapted to be in light-communication with fiber optic cable 221 disposed upon the distal surface [203 surface] of the implant. The tynes 223 disposed upon the distal portion 224 of the fiber optic cable receive the light and transmit the light to the adjacent brain tissue.

Now referring to FIG. 6, there is provided a second exemplary UV unit having an internal light source. Externally based-control device 222 has an RF energy source [224] *225* and an antenna 230 for transmitting signals to an internally-based antenna 232 provided on the prosthesis. These antennae 230, 232 may be electro-magnetically coupled to each other. The internal antenna 232 sends electrical power to a light emitting diode (LED) 234 disposed internally on the implant in response to the transmitted signal transmitted by the external antenna 230. The light generated by the LED travels across UV transparent casing 25 and into the brain tissue BT.

In some embodiments, and now referring to FIG. 7, the prosthesis having an internal light source further contains an internal power source 300, such as a battery (which could be re-chargeable), which is controlled by an internal receiver and has sufficient energy stored therein to deliver electrical power to the light source 234 in an amount sufficient to cause the desired light output.

When the implant is coupled with external energy, power can be transmitted into the internal device to re-charge the battery.

In some embodiments, the light generated by the implant is powered by wireless telemetry integrated onto or into the implant itself. In the FIG. 6 embodiment, the LED 234 may comprise a radiofrequency-to-DC converter and modulator. When radiofrequency signals are emitted by the external antenna 230 and picked up by the internal antenna 232, these signals are then converted by the receiver (not shown) into electrical current to activate the light source of the PCO unit.

In one embodiment, the implant may have an internal processor adapted to intermittently activate the LED.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include those available from Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strainlink™ device. Conventional transmitter-receiver telemetry is capable of transmitting up to about 500 milliwatts of energy to the internally-based antenna.

Figure 8:
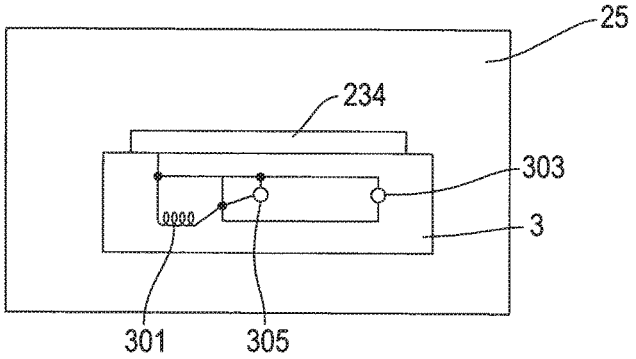

In some embodiments, and now referring, to FIG. 8, the implant includes a light emitting diode (LED) 234 built upon a base portion 3 of the implant, along with the required components to achieve trans-dermal activation and powering of the device. These components can include, but are not limited to, RF coils 301, control circuitry 303, a battery 305, and a capacitor. Such a device could be capable of intermittent or sustained activation without penetrating the skin, thereby avoiding trauma to the patient and/or risk of infection from skin-borne bacteria. As shown above, the accessory items needed to power and control the LED may be embedded within the implant. However, they could also be located on the surface(s) of the implant, or at a site adjacent to or near the implant, and in communication with the implant.

In some embodiments, the UV light source has a spectral maximum in the range of the UV and near-UV components of the solar spectrum. Preferably, the light source has a spectral maximum in the range of the UV components of the solar spectrum. Preferably, the light source has a spectral maximum in the range of less than about 380 nm, and is preferably between 280 nm and 320 nm. In some embodiments, the light source has a spectral maximum of about 311 nm-312 nm.

In some embodiments, the light source is provided on the implant and is adapted to be permanently implanted into the patient. The advantage of the internal light source is that there is no need for further transcutaneous invasion of the patient. Rather, the internally-disposed light source is activated by either a battery disposed on the implant, or by telemetry, or both. In some embodiments of the present invention using an internal light source, the light source is provided by a bioMEMs component. In one embodiment thereof, the internal light source comprises a UV light source, and preferably comprises an AlGaN substrate. It has been reported by Stutzmann, Diamond and Related Materials, 11(2002) 886-891, that AlGaN may have future application as a biosensor. Stutzman further conducted studies on the biocompatibility of GaN, AlGaN and AlN, and found very little interaction with living cell tissue, thereby suggesting the biocompatibility of these materials.

Figure 9:
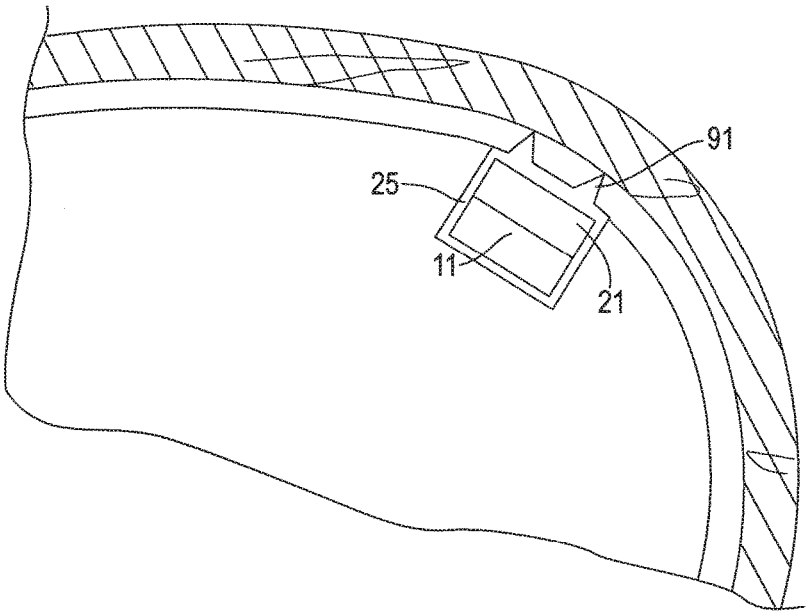
FIG. 9 is a representation of an anchored device of the present invention.

Because use of the present invention may require its repeated activation by Rf energy, it would be helpful if the user could be guaranteed that the implant remained in the same place within the skull. Accordingly, in some embodiments, and now referring to FIG. 9, the device of the present invention comprises anchors 91, preferably projecting from the casing 25. Preferably, the anchors are placed on the proximal side of the device, adjacent the antenna 21. In this position, the anchor may be inserted into the bone of the skull S, thereby insuring its position.

In some embodiments, it may be advantageous to combine the autologous production of IL-10 with an administration of exogenous IL-10. The exogenous IL-10 provides the benefit of a) insuring immediate IL-10 activity, and b) possibly super-inducing the production of the autologous IL-10.

In some embodiments of the present invention, UV irradiation causes sufficient IL-10 production to produce a local IL-10 concentration of at least 0.1 ng/ml. Shreedhar, J. Immunol., 1998, 260, 3783-9, reports producing 313 pg IL-10/ml by exposing keratinocytes to 0.02 J/cm$^2$ UV light, while Kang, J. Immunol., 1994, 153, 5256 reports producing 333 pg/ml in a supernatant from CD11b+macrophages exposed to 4 MEDs of UV light.

In some embodiments of the present invention, UV irradiation causes sufficient IL-10 production to produce a local IL-10 concentration of at least 1 ng/ml. Shreedhar, J. Immunol., 1998, 260, 3783-9, reports producing about 1.7 ng/ml of IL-10 by exposing mice to 0.015 J/cm$^2$ of UV radiation and then injecting the mice with IgG. When a 1 ng/ml concentration is obtained, IL-10 significantly reduces DNA fragmentation (according to Strle, J. Neuroimmunology, 2002 January; 122, 1-2,9-19).

In some embodiments of the present invention, UV irradiation causes sufficient IL-10 production to produce a local IL-10 concentration of at least 10 ng/ml. When a 10 ng/ml concentration is obtained, IL-10 causes a 50% inhibition of microglial apoptosis (according to Strle, supra).

The choroid plexus is a portion of the brain located relatively adjacent the hippocampus. According to Serot, J. Neuroimmunology, 104(2000) 115-119, the choroid plexus epithelium is infiltrated with dendritic cells, and these dendritic cells can secrete IL-10. Serot, supra, hypothesizes that these dendritic cells act as a physiologic sentinel at the blood-brain barrier (BBB), contributing to the immunoprivileged status of the brain.

Since the UVB literature repeatedly reports that the production of IL-10 in macrophages can be stimulated by UVB light, it is reasonable to expect that UVB light can likewise stimulate the production of IL-10 from the dendritic cells located in and around the choroid plexus epithelium.

Therefore, in accordance with the present invention, there is provided a method of treating a neurodegenerative disease, comprising the steps of:

a) irradiating the choroid plexus of a patients with an effective amount of UVB light.

Because it is known that the choroid plexus produces cerebrospinal fluid, it is believed that UVB irradiation of the choroid plexus epithelium will provide IL-10 secretion from the local dendritic cells into cerebrospinal fluid (CSF). In some embodiments, this IL-10-enriched CSF will bathe its neighboring hippocampus, thereby providing a therapeutically effective amount of IL-10 to the hippocampus.

Therefore, in some embodiments, there is provided a treatment for AD, wherein UVB light is delivered to the choroid plexus in a dose effective to produce therapeutic amount of IL-10, which is then secreted into the CSF to provide neuroprotective and anti-inflammatory therapy to at least the choroids plexus, and preferably other portions of the brain.

In some embodiments of the present invention involving transcutaneous UVB light delivery, a UVB-transmissible implant is placed in the skin over the skull. In contrast to human tissue such as skin (which readily absorbs UVB light), this implant allows UVB light to pass from the surface of the scalp to the fiber optic implant based in the skull.

In some embodiments, the UVB-transmissible implant comprises a UVB-transmissible polymer. In other embodiments, the UVB-transmissible implant comprises a UVB-transmissible ceramic, such as glass. The glass content of the implant is preferably in the range of 20-40 volume percent ("v/o"). At higher glass glass contents, the implant becomes relatively inelastic. At lower implants, UVB transmission is more problematic. The UVB transmissible component of the implant may be in the form of beads, long fibers or chopped fibers. Each of these components, when embedded in a collagen matrix (such as SIS), can provide UVB transmissability while retaining the skin-like flexibility of the implant.

Therefore, there is provided a procedure wherein UVB light is delivered transcutaneously through a UVB transmissible implant (such as a glass fiber/SIS implant) to the top of the skull, where it is received by the proximal end of a fiber optic cable (which has been embedded in the skull), and finally delivered through the fiber optic cable to a predetermined portion of the brain (such as either the hippocampus or choroid plexus, or both).

In some embodiments, the implants of the present invention are adapted to deliver red light, either alone or in combination with UVB light.

It has been reported in the literature that near infra-red light saves neurons that have been challenged by neurotoxics from apoptosis. In particular, Wong-Riley, J. Biol. Chem. 2004, e-pub Nov. 22, reports that irradiating neurons with 670 nm red light significantly reduced neuronal cell death induced by 300 mM KCN from 83.6% to 43.5%.

The general concept of repairing brain cells through red light irradiation is also well supported by the literature. Wollman, Neurol. Res. 1998, July 20(5) 470-2 reports that providing daily 3.6 J/cm$^2$ doses of red light from a He—Ne laser to cortex explants resulting in a significant amount of sprouting of cellular processes outgrowth. Wollman concludes that the irradiation induces neurite processes sprouting and improves nerve tissue recovery. Similarly, Wollman, Neurol. Res. 1996 October 18(5) 467-70 reports the enhanced migration and massive neurite sprouting of cultured rat embryonal brain cells subject to an 8 minute dose of a 0.3 mW, He—Ne laser. Therefore, the red light of the present invention may further cause repair and regeneration of damaged nerve cells.

Therefore, it is expected that transmitting an effective amount of red light into the brain of an AD patient will have both neuroprotective and neuroregenerative effects upon the AD brain.

Therefore, in accordance with the present invention, there is provided a method of treating or preventing Alzheimer's disease, comprising the steps of:

a) providing an implant having a red light source,
b) positioning the implant within or adjacent to brain tissue, and
c) activating the light source to irradiate the brain tissue with an amount of red light.

Without wishing to be tied to a theory, it is believed that the therapeutic neuroprotective and neuroregenerative effects of red light described above may be due to a) an increase in ATP production in the irradiated neurons, and b) an increase in the activity of local anti-oxidant enzymes superoxide dismutase (SOD) and catalase.

It is believed that irradiating neurons in the brain with red light will likely increase ATP production from those neurons. Mochizuki-Oda, Neurosci. Lett. 323 (2002) 208-210, examined the effect of red light on energy metabolism of the rat brain and found that irradiating neurons with 4.8 W/cm$^2$ of 830 nm red light increased ATP production in those neurons by about 19%.

Without wishing to be tied to a theory, it is further believed that the irradiation-induced increase in ATP production in neuronal cell may be due to an upregulation of cytochrome oxidase activity in those cells. Cytochrome oxidase (also known as complex IV) is a major photoacceptor in the human brain. According to Wong-Riley, Neuroreport, 12:3033-3037, 2001, in vivo, light close to and in the near-infrared range is primarily absorbed by only two compounds in the mammalian brain, cytochrome oxidase and hemoglobin. Cytochrome oxidase is an important energy-generating enzyme critical for the proper functioning of neurons. The level of energy metabolism in neurons is closely coupled to their functional ability, and cytochrome oxidase has proven to be a sensitive and reliable marker of neuronal activity.

Importantly, the literature has made a direct association between defects in cytochrome c oxidase and Alzheimer's Disease. See, e.g., Cottrell, Neuropathol. Appl. Neurobiol. 2002, October 28(5) 3906; Cottrell, Neurology, July 24, 57(2) 260-4. Alieu, Neurol. Res., 2003, September 25(6) 665-74. Aliev, Ann NY Acad. Sci., 2002, November 977, 45-64.

By increasing the energetic activity of cytochrome oxidase, the energy level associated with neuronal metabolism may be beneficially increased. Indeed, the literature reports that red light reverses the inhibitory effects of neurotoxins upon cytochrome oxidase activity, leading to increased energy metabolism in neurons functionally inactivated by toxins. Wong-Riley Neuroreport 12(14) 2001:3033-3037 and Wong-Riley, J. Biol. Chem., e-pub, Nov. 22, 2004.

According to Kamanli, Cell Biochem. Func. 2004, 22:53-57, catalase detoxifies hydrogen peroxide and converts lipid hydroperoxides into non-toxic alcohols, and is essential for the inhibition of inflammation related to the function of neutrophils.

Romm, Biull. Eksp. Biol. Med. 1986 October 102(10) 426-8 reports that laser irradiation of wounds results in a decreased chemiluminescence that is attributable to activation of catalase in the tissue fluid.

Therefore, it is believed that irradiating the AD brain with an effective amount of red light will therapeutically increase of the activity of catalase in the irradiated region, thereby attenuating the deleterious effect of hydrogen peroxide upon the neurons in the AD brain.

According to Kamanli, supra, SOD catalyses dismutation of the superoxide anion into hydrogen peroxide.

The literature repeatedly reports that red light irradiation of inactivated SOD increases its activity. For example, Vladimirov, Biochemistry (Moscow) 69(1) 2004, 81-90 provides a review including the photoreactivation of Cu—Zn SOD under He—Ne laser. Karu, Laser Ther. 1993, 5, 103-9 reports that reactive oxygen species in human blood were found to be suppressed after laser diode illumination at 660 nm, 820 nm, 880 nm and 950 nm. This affect has been attributed by other authors to the activation of SOD or catalase. Volotovskaia Vopr Kurortol Zizioter Lech Fiz Kult 2003 May-June (3)22-5 reports that 632 nm He—Ne laser irradiation of blood has an anti-oxidant effect as shown by activation of SOD. Ostrakhovich Vestn Ross Akad Med Nauk. 2001(5) 23-7 reports that infrared pulse laser therapy of RA patients caused an increase in SOD activity. Gorbatenkova Biofizika, 1988 July-August 33(4) 717-9 reports that SOD that was inactivated by hydrogen peroxide was reactivated by a 450-680 m red light laser. Vladimirov, Free Rad. Biol. Med. 1988, 5(5-6) 281-6 reports the inactivation of SOD by its incubation in a low pH 5.9 solution and its subsequent reactivation by helium-neon laser light. Catalase was found to be reactivated as well. Cho, In Vivo, 2004, September-October 18(5) 585-91 reports on the use of low level laser therapy (LLLT) to treat knee joints that have been induced with OA by injection of hydrogen peroxide. SOD was reported to increase about 40% in the OA group as compared to controls.

Therefore, it is believed that irradiating the AD brain with an effective amount of red light will therapeutically increase of the activity of SOD in the irradiated region, thereby attenuating the deleterious effect of superoxide anion upon the neurons in the AD brain.

According to Leung, Laser Surg. Med. 31:283-288 (2002), nitric oxide enhances oxidative insult by reacting with superoxide anion to form a stronger oxidant, peroxynitrite, which leads to mitochondrial dysfunction, DNA damage and apoptosis. Haas, Neuroscience Letters, 322, (2002) 121-126 reports that iNOS is induced by amyloid plaques in AD brains, and is responsible for producing NO, which is considered to be highly neurotoxic when generated in excess.

Leung, supra, investigated the effect of low energy red laser after stroke in rats, and found that red light can suppress NO synthase activity. In particular, Leung found that irradiating a portion of the rat's brain with a 660 nm red light (average power 8.8 mW, 2.64 J/cm$^2$) reduced NOS activity up to about 80% over that in unirradiated stroke rats, and up to about 60% over the NOS activity in normal rats. Leung concluded that the main findings of the study was that low energy laser may be protective by suppressing the activity of NOS in cerebral ischemia and reperfusion.

Without wishing to be theory, it is believed that irradiation of a portion of an Alzheimer's brain will similarly therapeutically suppress NO synthase activity, thereby attenuating peroxynitrite activity.

It is noted that Leung, supra, also reported that red light irradiation of the brain resulted in a TGF-B tissue concentration of 1-6 ng/ug protein of tissue. Thus, red light irradiation of the OB may very well be an attractive non-invasive way of generating large amounts of TGF-B within the brain.

Moreover, the literature has reported other highly beneficial effects of red light, including its attenuation of the immune response following neuronal injury. Byrnes, Lasers Surg. Medicine 9999:1-15(2005) reports that 810 nm light promotes the regeneration and functional recovery of the injured spinal cord, and significantly suppressed IL-6 and iNOS expression and immune cell activation. Of note, Byrnes reports a 171-fold decrease in IL-6 expression and an 80% reduction in iNOS expression when the spinal cord lesion was irradiated on a daily basis with about 100 J/cm$^2$ red light for about 2 weeks.

The ability of red light to suppress IL-6 in injured neuronal matter is important to the present invention because IL-6 is thought to play a major role in AD pathology. For example, Del Bo, Neuroscience Letters 188 (1995) 70-74 reports that IL-6 increased mRNA levels of beta-amyloid precursor protein (APP) in a dose dependent relationship. Qiu, J. Neuroimmunolog, 139, (2003) 51-57 reports that IL-6 is thought to contribute to AD by increasing amyloidogenesis. Huell, Acta Neuropathol. (Berl) 1995; 89(6) 544-51 reports that IL-6 is found in early stages of plaque formation and is restricted to the brain of AD patients. In sum, it appears that IL-6 plays and early role in the pathology of AD. Therefore, reducing the IL-6 expression in and around AD lesions may be quite helpful.

Also without wishing to be tied to a theory, it is further believed that red light may also be effective in causing the release of calcitonin gene related peptide (CGRP), which in turn may cause mast cells to degranulate and release IL-10, thereby attenuating AD.

Because long wavelength red light can penetrate soft tissue up to many centimeters, it might be advantageous to transcutaneously deliver the red light to the fiber optic. Now referring to FIGS. 10a-10c, in one embodiment, a fiber optic 401 having a proximal light collector 403 is placed at the interior rim of the skull and the distal end portion 405 of the cable (which is unclad) is run to the target location. Red light can then be delivered transcutaneously from a probe 415 to the collector 403, which will then transport the light to the target location.

Figure 10C:
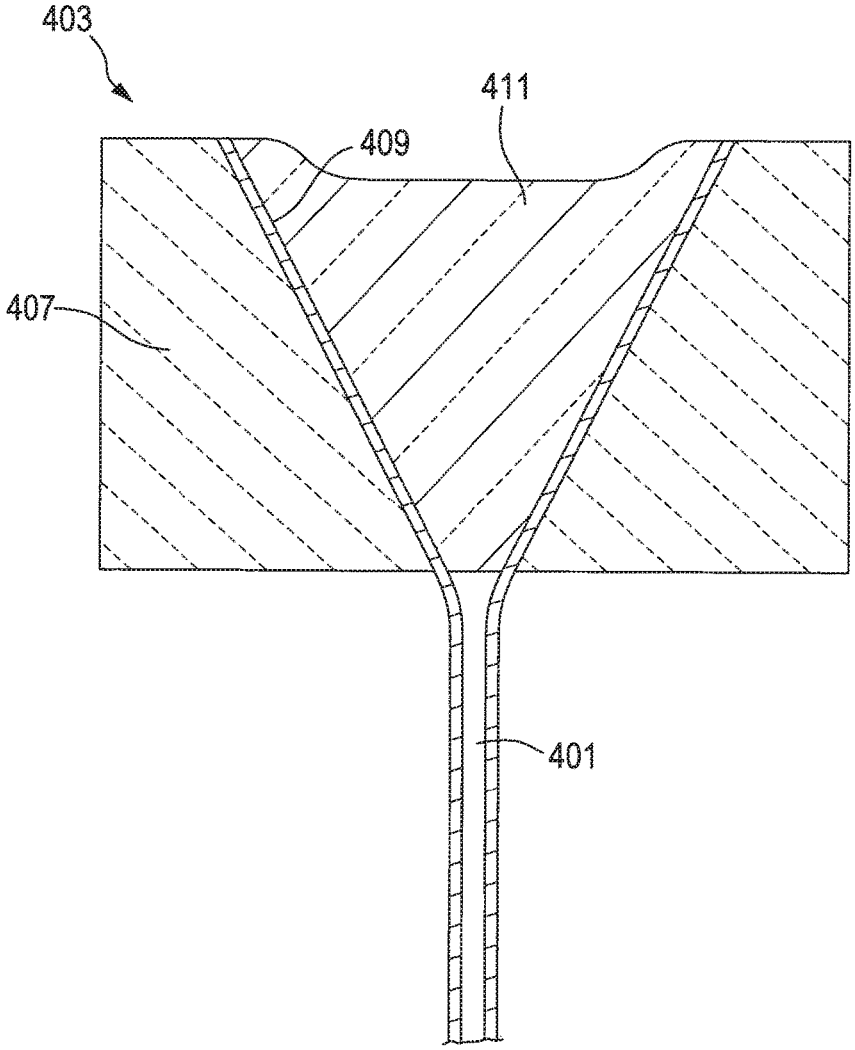
FIG. 10C is a cross-section of a fiber optic implant of the present invention.

In some embodiments, as in FIG. 10c, the collector 403 has a porous osteoconductive collar 407 for intergrating with the bone in the skull. The collector may comprise a funnel-shaped mirror 409 (made of titanium) that connects to the fiber optic cable 401 and is filed with a red light-transparent material 411 such as silica.

To enhance the propagation of light emitted from the end of the fiber, a lens could be placed at the distal end of the fiber to spread the light, or a diffuser such as a small sheet or plate of optical material could be used to create more surface area. Alternatively, one could create a series of lateral diffusers, such as grooves or ridges, along the distal portion of end of the fiber to spread light out from 360 degrees perpendicular to the axis of the fiber, as well as emanating directly out from the end of the fiber.

In some embodiments, the devices shown in FIGS. 1-9 may be modified to deliver red light alone, or a combination of red and UV light.

Preferably, the red light is provided in a wavelength of between 600 nm and 1000 nm. Preferably, the red light of the present invention has a wavelength of between about 650 nm and about 1000 nm. In some embodiments, the wavelength of light is between 800 and 900 nm, more preferably between 800 nm and 835 nm. In this range, red light has not only a large penetration depth (thereby facilitating its transfer to the fiber optic and SN), but Wong-Riley reports that cytochrome oxidase activity is significantly increased at 830 nm, and Mochizuki-Oda reported increased ATP production via a 830 mn laser.

In some embodiments, the wavelength of light is between 600 and 700 nm. In this range, Wong-Riley reports that cytochrome oxidase activity was significantly increased at 670 nm. Wollman reports neuroregenerative effects with a 632 nm He—Ne laser.

Respecting penetration depths, Byrnes, Lasers Surg. Medicine 9999:1-15(2005) reports that an effective amount of 810 nm light was able to traverse a 1 cm thick rat spinal cord. The penetration depths of various wavelengths of red light in grey matter brain tissue have been reported in Yaroslavsky, Phys. Med. Biol. 47(2002) 2059-73 as follows:

| Wavelength | Penetration Depth |
|---|---|
| 630 nm | 0.83-4.06 |
| 675 nm | 1.29 |
| 670 nm | 4.4 |
| 1064 nm | 1.18-3.28 |

In some embodiments, the light source is situated to irradiate adjacent tissue with between about 0.02 J/cm$^2$ and 200 J/cm$^2$ energy. Without wishing to be tied to a theory, it is believed that light transmission in this energy range will be sufficient to increase the activity of the cytochrome oxidase and anti-oxidant activity around and in the target region. In some embodiments, the light source is situated to irradiate adjacent tissue with between about 0.2 J/cm$^2$ and 50 J/cm$^2$ energy, more preferably between about 1 J/cm$^2$ and 10 J/cm$^2$ energy. In other embodiments, the red light is delivered in an amount of greater than 10 J/cm$^2$.

In some embodiments, the light source is situated to produce an energy intensity of between 0.1 watts/cm$^2$ and 10 watts/cm$^2$. In some embodiments, the light source is situated to produce about 1 milliwatt/cm$^2$.

Of note, it has been reported that the neuroprotective effects of red light can be effected by a single irradiation on the order of minutes. Wong-Riley, J. Biol. Chem. 2004, e-pub Nov. 22, reports that irradiating neurons with 670 nm red light for only ten minutes results in neuroprotection. Similarly, Wong-Riley Neuroreport 12(14) 2001:3033-3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme".

Therefore, in some embodiments of the present invention, the therapeutic dose of red light is provided on approximately a daily basis, preferably no more than 3 times a day, more preferably no more than twice a day, more preferably once a day.

In some embodiments, the red light irradiation is delivered in a continuous manner. In others, the red light irradiation is pulsed in order to reduce the heat associated with the irradiation. Without wishing to be tied to a theory, it is believed that pulsed light may be more effective in achieving the vibratory oscillation of the catalase and SOD molecules.

In some embodiments, red light is combined with polychrome visible or white light.

In some embodiments, the fiber optic is placed to irradiate a portion of the AD brain damaged by a beta-amyloid plaque. In some embodiments, the fiber optic is placed to irradiate a portion of the AD brain undamaged by a beta-amyloid plaque. In some embodiments, the fiber optic is placed to irradiate a portion of the hippocampus, the amygdala, the locus coeruleus, or the prefrontal cortex, or combinations thereof.

Therefore, in general, the fiber optic may be placed within about an 4-10 mm of these targeted locations. The surgeon may access the selected location though the brain parenchyma using stereotactic MRI guidance. As it is desirable to use a flexible material as the fiber optic in order to reduce migration, the distal end of the fiber optic may be placed near the selected target with the help of a relatively stiff introducer cannula.

In some embodiments, the patient can receive a unilateral fiber optic, while in other the patient can receive bilateral fiber optic. In some embodiments, a plurality of cables is used to deliver light to each target region.

In some embodiments, a red light source or red light collector and the proximal end of the fiber optic are placed in the chest. This allows the surgeon to conduct maintenance activity on an implanted light source without having to re-open the cranium. In addition, location within the chest also lessens the chances of surface erosion.

According to Johanson, Cell. Mol. Neurobiol., 20(2) 2000, 197-216, the choroid plexus epithelium is a site of synthesis of both bFGF and TGF-β. Each of these growth factors may provide neuroprotection to neurons in Alzheimer's Disease. For example, Each of Ren, Brain. Res. 1996, Sept. 2, 732 (1-2) 16-24 and Prehn, Mol. Pharm. 1996, February 49(2) 319-28 reports that TGF-beta exerts a neuroprotective effect against beta amyloid neurotoxicity in hippocampal neurons.

At the same time, the laser literature repeatedly reports that bFGF and TGF-B expression in cells can be stimulated by low level red light. For example, Leung, Lasers Surg. Med. 2002, 31, (4) 283-8 reports the novel expression of TGF-B in ischemic brain tissue exposed to red light, while Nowak, Plast. Reconstr. Surg., 2000 May 105(6), 2039-48 reports the expression of both TGF-B and bFGF in normal dermal fibroblasts exposed to red light. Therefore, it is reasonable to expect that low level red laser light may likewise stimulate the production of these growth factors from the choroid plexus epithelium.

Therefore, in accordance with the present invention, there is provided a method of treating a neurodegenerative disease, comprising the steps of:

b) irradiating the choroid plexus of a patients with an effective amount of red light.

Because it is known that the choroid plexus produces cerebropspinal fluid (CSF) which bathes the entire brain, it is believed that irradiation of the choroid plexus epithelium will result in the expression of bFGF and TGF-β in the choroid plexus, and its secretion therefrom into the cerebrospinal fluid (CSF). In some preferred embodiments, this cytokine-enriched CSF will contain enough of these growth factors to therapeutically bathe its neighboring hippocampus in at least one of bFGF and TGF-B.

Therefore, in some embodiments, there is provided a treatment for AD, wherein UVB and red lights are delivered to the choroid plexus in doses effective to produce therapeutic amounts of IL-10, bFGF and TGF-β, which are then secreted into the CSF to provide neuroprotective and anti-inflammatory therapy to at least the hippocampus portion of the brain.

It is well known in the art that AD is characterized not only by the presence of macrophage-like microglia, but also by the presence of lymphocytes. Since it is also known that lymphocytes may secrete pro-inflammatory cytokines via the Th1 pathway, it is appropriate to consider the activity of these T cells in AD therapies.

U.S. Pat. No. 6,083,919 (Johnson) has reported the co-administration of IL-10 and TGF-β in amounts effective to produce a synergistic reduction in lymphocyte activity. In one example, Johnson reports that about 0.3 ng/ml of each of IL-10 and TGF-β inhibits the activation of self-reactive T cells in autoimmune diseases from 20,000 units to less than 500 units (a 97% reduction). This amounts to about a 10-fold reduction in activation over either cytokine acting alone at 0.3 ng/ml.

Therefore, in one embodiment with the present invention, there is provided a method of treating AD, wherein both IL-10 and TGF-B are administered in amounts effective to produce a synergistic reduction in lymphocyte activity. In some preferred embodiments, the IL-10 is provided by UVB irradiation of local microglia or of dendritic cells adjacent the choroid plexus, and the TGF-B is provided by red light irradiation of the choroid plexus epithelium.

Therefore, delivering both red and UVB light through the same fiber optic to either place, and produce IL-10, bFGF and TGF-B at either place to provide therapy for an AD patient without the need for a diode implant.

In some embodiments, a graft containing fibroblasts is placed within the zone or irradiation of the red light fiber optic. When so irradiated, the fibroblasts will secrete bFGF.

Although the above devices offer the advantage of requiring only a single invasive procedure, there may be situations wherein multiple invasions of the skull are considered acceptable. In those situations, it may be acceptable to simply deliver exogenous IL-10 locally to the inflamed tissue. If multiple invasions are considered acceptable, then, in another aspect of the present invention, there is also provided a method of treating or preventing Alzheimer's disease, comprising the step of:

a) intracerebroventricularly administering an effective amount of Il-10.

Intracerebroventricularly administration of an effective amount of Il-10 is a desirable procedure because the surgeon may conveniently obtain and deliver exogenous Il-10 and thereby not rely upon the patient's immune system to produce the IL-10. Furthermore, intracerebroventricularly administration of an effective amount of Il-10 can be conveniently carried out via an injection through the skull of the patient.

In some embodiments, the intracerebroventricularly administered IL-10 is provided in a sustained release device. The sustained release device is adapted to remain within the brain tissue for a prolonged period and slowly release the IL-10 contained therein to the surrounding environment. This mode of delivery allows an IL-10 to remain in therapeutically effective amounts within the brain tissue for a prolonged period.

In some embodiments, the IL-10 is predominantly released from the sustained delivery device by its diffusion through the sustained delivery device (preferably, though a polymer). In others, the IL-10 is predominantly released from the sustained delivery device by the biodegradation of the sustained delivery device (preferably, biodegradation of a polymer). In some embodiments thereof, and now referring to FIG. 10, the implant 401 comprises IL-10 (403) embedded in a polymer 405, such as PLA.

Preferably, the sustained release device comprises a bioresorbable material whose gradual erosion causes the gradual release of the IL-10 to the brain tissue environment. In some embodiments, the sustained release device comprises a bioresorbable polymer. Preferably, the bioresorbable polymer has a half-life of at least six months, more preferably at least nine months, more preferably at least 12 months.

In some embodiments, the sustained release device provides controlled release. In others, it provides continuous release. In others, it provides intermittent release. In others, the sustained release device comprises a biosensor.

A. K. Burkoth, Biomaterials (2000) 21:2395-2404, the entire teaching of which are incorporated herein by reference, discloses a number of photopolymerizable anhydrides suitable as sustained release devices. The repeating unit of these anhydrides comprises a pair of diacid molecules linked by anhydride bonds that are susceptible to hydrolysis. Because the diacid molecules are hydrophobic, there is a limited diffusion of water into the polymer, and so the polymer is subject only to surface degradation (not bulk degradation). This is advantageous because the lifetime of the polymer will essentially correspond to the mass of the polymer.

In some embodiments, the photopolymerized anhydride is selected from the group consisting of polymers of methacrylated sebacic acid (MSA), methacrylated 1,6-bis(p-carboxyphenoxy) hexane (MCPH), 1,3-bis(p-carboxyphenoxy) propane (CPP), methacrylated cholesterol (MC), methacrylated stearic acid (MstA) and blends and copolymers therefrom.

In one embodiment, a copolymer of poly[bis(p-carboxyphenoxy) propane] anhydride and sebacic acid in a 50:50 to 20:80 formulation is used as the sustained release device.

In some embodiments, the photopolymerization is carried out by adapting a light source to the distal end of the delivery cannula that enters the cranium. In other embodiments, a photo-optic cable is used to transmit light energy into the precursor components that have been deposited in the brain. In other embodiments, light is transmitted through the skin (i.e, transcutaneously). In some embodiments thereof, a photobleaching initiating system is used.

In some embodiments, a linear polyanhydride is first dissolved in a monomer, and then photopolymerized to form a S-IPN of a photopolymerized anhydride. These are particularly desirable where increased resistance to hydroysis is desired. Accordingly, in some embodiments, the composition of the present invention comprises a S-IPN comprising a photopolymerized anhydride.

In some embodiments, poly (1,6-bis (p-carboxyphenoxy) hexane (PCPH) is used. This polymer has a degradation of about 496 days, and so is desirably used as the composition of the present invention.

Polymerization is preferably initiated using photoinitiators. Photoinitiators that generate an active species on exposure to UV light are well known to those of skill in the art. Active species can also be formed in a relatively mild manner from photon absorption of certain dyes and chemical compounds.

These groups can be polymerized using photoinitiators that generate active species upon exposure to UV light, or, preferably, using long-wavelength ultraviolet light (LWUV) or visible light. LWUV and visible light are preferred because they cause less damage to tissue and other biological materials than UV light. Useful photoinitiators are those, which can be used to initiate polymerization of the macromers without cytotoxicity and within a short time frame, minutes at most and most preferably seconds.

Exposure of dyes and co-catalysts such as amines to visible or LWUV light can generate active species. Light absorption by the dye causes the dye to assume a triplet state, and the triplet state subsequently reacts with the amine to form an active species, which initiates polymerization. Polymerization can be initiated by irradiation with light at a wavelength of between about 200-700 nm, most preferably in the long wavelength ultraviolet range or visible range, 320 nm or higher, and most preferably between about 365 and 514 nm.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

Photopolymerization of these polymer solutions is based on the discovery that combinations of polymers and photoinitiators (in a concentration not toxic to the cells, less than 0.1% by weight, more preferably between 0.05 and 0.01% by weight percent initiator) will crosslink upon exposure to light equivalent to between one and three mWatts/$cm^2$ applied to the skin of nude mice.

In some embodiments, the sustained delivery device comprises bioerodable microspheres. The IL-10 is preferably contained in a gelatin (or water or other solvent) within the capsule, and is released to the brain tissue environment when the outer shell has been eroded. The device can include a plurality of capsules having outer shells of varying thickness, so that the sequential breakdown of the outer shells provides periodic release of the IL-10.

In some embodiments, the sustained delivery device comprises an inflammatory-responsive delivery system, preferably comprising bioerodable microspheres that are eroded by invading macrophages. This technology provides a high correspondence between physiologic inflammation of brain tissue environment and the release of the IL-10 into that environment. Preferably, the technology disclosed in Brown et al., Arthritis. Rheum. 1998 December; 41(12) pp., 2185-95 is selected.

In some embodiments thereof the IL-10 is delivered through a drug pump. In some embodiments, the sustained delivery device comprises the devices disclosed in U.S. Pat. No. 5,728,396 ("Peery"), the specification of which is incorporated by reference in its entirety.

In some embodiments, the sustained, delivery device comprises a plurality (preferably at least one hundred) of water-containing chambers, each chamber containing IL-10. Each chamber is defined by bilayer lipid membranes comprising synthetic duplicates of naturally occurring lipids. The release of the Il-10 can be controlled by varying at least one of the aqueous excipients, the lipid components, and the manufacturing parameters. Preferably, the formulation comprises-no more than 10% lipid. In some embodiments, the Depofoam™ technology of Skyepharma PLC (located in London, United Kingdom) is selected.

In some embodiments, the sustained delivery device comprises a delivery system disclosed in U.S. Pat. No. 5,270,300 ("Hunziker"), the specification of which is incorporated by reference in its entirety.

In some embodiments, the sustained delivery device comprises the co-polymer poly-DL-lactide-co-glycolide (PLG). Preferably, the formulation is manufactured by combining the IL-10, the co-polymer and a solvent to form a droplet, and then evaporating the solvent to form a microsphere. The plurality of microspheres are then combined in a biocompatible diluent. Preferably, the IL-10 is released from the co-polymer by its diffusion therethrough and by the biodegradation of the co-polymer. In some embodiments hereof, the ProLease™ technology of Alkermes (located in Cambridge, Mass.) is selected.

Hydrogels can also be used to deliver the IL-10 in a time-release manner to the brain tissue environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or crosslinking. The hydrogels employed in this invention rapidly solidify to keep the IL-10 at the application site, thereby eliminating undesired migration from the brain tissue. The hydrogels are also biocompatible, e.g., not toxic, to cells suspended in the hydrogel.

A "hydrogel-IL-10 composition" is a suspension of a hydrogel containing desired IL-10. The hydrogel-IL-10 composition forms a uniform distribution of IL-10 with a well-defined and precisely controllable density. Moreover, the hydrogel can support very large densities of IL-10. In addition, the hydrogel allows diffusion of nutrients and waste products to, and away from, the IL-10, which promotes tissue growth.

Hydrogels suitable for use in the present invention include water-containing gels, i.e., polymers characterized by hydrophilicity and insolubility in water. See, for instance, "Hydrogels", pages 458-459 in Concise Encyclopedia of Polymer Science and Engineering, Eds. Mark et al., Wiley and Sons, 1990, the disclosure of which is incorporated herein by reference. Although their use is optional in the present invention, the inclusion of hydrogels is preferred since they tend to contribute a number of desirable qualities. By virtue of their hydrophilic, water-containing nature, hydrogels can house viable cells, such as mesenchymal stems cells.

In a preferred embodiment, the hydrogel is a fine, powdery synthetic hydrogel. Suitable hydrogels exhibit an optimal combination of such properties as compatibility with the matrix polymer of choice, and biocompatability. The hydrogel can include any of the following: polysaccharides, proteins, polyphosphazenes, poly(oxyethylene)-poly(oxypropylene) block polymers, poly(oxyethylene)-poly (oxypropylene) block polymers of ethylene diamine, poly (acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly (phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In some embodiments, the sustained delivery device includes a polymer selected from the group consisting of PLA, PGA, PCL, and mixtures thereof.

In other embodiments, the IL-10 is administered intrathecally.

In other embodiments, there is provided a method of treating Alzheimer's disease, comprising the step of:

a) intracerebroventricularly administering an effective amount of Il-4 to a patient.

In other embodiments, there is provided a method of treating Alzheimer's disease, comprising the step of:

a) intracerebroventricularly administering an effective amount of an immunoglobulin selected from the group consisting of IgG and IgA to a patient.

In addition to Alzheimer's Disease, it is believed that the devices of the present invention would also be effective in treating other inflammatory mediated diseases of the central nervous system, including Infection (Viral, Bacterial, Protozoal, Prion, Fungal), AIDs-related Alzheimer's Disease, Multiple Sclerosis, Devic's disease and ADEM Sarcoidosis, Acute brain injury, Auto-immune diseases and vasculitides, and Paraneoplastic syndromes.

Modifications of the IL-10 and its functional fragments that either enhance or do not greatly affect the ability to inhibit oxidation are also included within the term "IL-10." Such modifications include, for example, additions, deletions or replacements of one or more amino acids from the native amino acid sequence of IL-10 with a structurally or chemically similar amino acid or amino acid analog. These modifications will either enhance or not significantly alter the structure, conformation or functional activity of the IL-10 or a functional fragment thereof. Modifications that do not greatly affect the activity of the IL-10 or its functional fragments can also include the addition or removal of sugar, phosphate or lipid groups as well as other chemical derivations known in the art. Additionally, IL-10 or its functional fragments can be modified by the addition of epitope tags or other sequences that aid in its purification and which do not greatly affect its activity.

As used herein, the term "functional fragment," in connection with IL-10, is intended to mean a portion of the IL-10 that maintains the ability of the IL-10 to inhibit inflammation. A functional fragment can be, for example, from about 6 to about 300 amino acids in length, for example, from about 7 to about 150 amino acids in length, more preferably from about 8 to about 50 amino acids in length. If desired, a functional fragment can include regions of the IL-10 with activities that beneficially cooperate with the ability to inhibit inflammation.

We claim:

1. A method of treating a patient having Alzheimer's Disease, comprising the steps of:

a) providing a device comprising an LED and a fiber optic cable having a proximal end portion and a distal end portion;

b) implanting the device into the patient so that the distal end portion of the fiber optic cable is located adjacent to the hippocampus, and c) delivering light provided in a wavelength of between 600 nm and about 1000 nm from the LED through the proximal end portion of the fiber optic cable to the distal end portion of the cable, and d) irradiating the hippocampus with an effective amount of the delivered light, wherein the fiber optic cable and LED are located inside the patient's skull, wherein the distal end portion of the fiber optic cable does not directly contact the hippocampus.

2. A method of treating a patient having Alzheimer's Disease, comprising the steps of:

a) providing a device comprising an LED and a fiber optic cable having a proximal end portion and a distal end portion;

b) implanting the device into the patient so that the distal end portion of the fiber optic cable is located adjacent to the hippocampus, and c) delivering light provided in a wavelength of between 650 nm and about 1000 nm from the LED through the proximal end portion of the fiber optic cable to the distal end portion of the cable, and d) irradiating the hippocampus with an effective amount of the delivered light, wherein the fiber optic cable and LED are located inside the patient's skull, wherein the distal end portion of the fiber optic cable does not directly contact the hippocampus.

*3. A method of treating a patient having Alzheimer's Disease, comprising the steps of:*

*a) selecting a device comprising an LED and a light emitter having a proximal end portion and a distal end portion;*

*b) inserting at least a portion of the device into the patient so that the distal end portion of the light emitter is located between the patient's skin and hippocampus and placed to irradiate a portion of the hippocampus, and*

*c) delivering light provided in a wavelength of between 600 nm and about 1000 nm from the LED through the proximal end portion of the light emitter to the distal end portion of the light emitter,*

*d) irradiating the hippocampus with an effective amount of the delivered light, and*

*e) placing the distal end portion of the light emitter within 10 mm of the hippocampus wherein the distal end portion of the light emitter does not directly contact the hippocampus.*

*4. The method of claim 3, wherein delivering light provided in a wavelength of between 600 nm and about 1000 nm includes delivering light provided in a wavelength of between 600 nm and 700 nm.*

*5. The method of claim 3, wherein delivering light provided in a wavelength of between 600 nm and about 1000 nm includes delivering light provided in a wavelength of between 800 nm and 900 nm.*

*6. The method of claim 3, wherein delivering light provided in a wavelength of between 600 nm and about 1000 nm includes delivering light provided in a wavelength of between 800 nm and 835 nm.*

*7. The method of claim 3, wherein the hippocampus is irradiated with between about 0.2 J/cm$^2$ and 200 J/cm$^2$ of energy.*

*8. The method of claim 3, wherein the hippocampus is irradiated with between about 0.2 J/cm$^2$ and 50 J/cm$^2$ of energy.*

*9. The method of claim 3, wherein the hippocampus is irradiated with between about 1 J/cm$^2$ and 10 J/cm$^2$ of energy.*

*10. The method of claim 3, wherein the hippocampus is irradiated for a time on the order of minutes.*

*11. The method of claim 3, wherein the hippocampus is irradiated for 10 minutes.*

*12. The method of claim 3, further comprising intracerebroventricularly administering an effective amount of Il-10.*

*13. The method of claim 3, further comprising administration of UVB irradiation.*

*14. The method of claim 3, further comprising placing the distal end portion of the light emitter within 4 mm of the hippocampus.*

* * * * *